(12) United States Patent
O'Neill et al.

(10) Patent No.: US 10,968,167 B2
(45) Date of Patent: Apr. 6, 2021

(54) 2,2,2-TRIFLUOROACETIC ACID 1-(2,4-DIMETHYLPHENYL)-2-[(3-METHOXYPHENYL)-METHYLENE] HYDRAZIDE POLYMORPHS AND METHOD OF MAKING THE SAME

(71) Applicant: Abrexa Pharmaceuticals, Inc., San Diego, CA (US)

(72) Inventors: Michael O'Neill, Concord, OH (US); Barbara Kidon, Concord, OH (US); William A. Janz, Concord, OH (US); Hongqiao Wu, Broadview Heights, OH (US)

(73) Assignee: ABREXA PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 16/975,054

(22) PCT Filed: Feb. 20, 2019

(86) PCT No.: PCT/US2019/018835
§ 371 (c)(1),
(2) Date: Aug. 21, 2020

(87) PCT Pub. No.: WO2019/164997
PCT Pub. Date: Aug. 29, 2019

(65) Prior Publication Data
US 2020/0399205 A1 Dec. 24, 2020

Related U.S. Application Data

(60) Provisional application No. 62/633,441, filed on Feb. 21, 2018.

(51) Int. Cl.
*C07C 249/16* (2006.01)

(52) U.S. Cl.
CPC ........ *C07C 249/16* (2013.01); *C07B 2200/13* (2013.01)

(58) Field of Classification Search
CPC .................................................... C07C 249/16
See application file for complete search history.

(56) References Cited

FOREIGN PATENT DOCUMENTS

WO     2009/052116 A1     4/2009

OTHER PUBLICATIONS

Patent Cooperation Treaty, International Search Report for PCT/US2019/018835, dated Jun. 19, 2019, pp. 1-4.
Prior, et al., The neurotrophic compound J147 reverses cognitive impairment in aged Alzheimer's disease mice, Alzheimer's Research & Therapy, 2013, pp. 1-19, vol. 5(25).
Chen et al., A Novel Neurotrophic Drug for Cognitive Enhancement and Alzheimer's Disease, PLoS One, Dec. 2011, pp. 1-17, vol. 6(12).
Daugherty et al., A novel Alzheimer's disease drug candidate targeting inflammation and fatty acid metabolism, Alzheimer's Research & Therapy, 2017, pp. 1-17, vol. 9(50).

*Primary Examiner* — Brian J Davis
(74) *Attorney, Agent, or Firm* — Pillsbury Winthrop Shaw Pittman, LLP

(57) ABSTRACT

Crystalline polymorph forms of neurotrophic agent 2,2,2-trifluoroacetic acid 1-(2,4-Dimethylphenyl)-2-[(3-methoxyphenyl)methylene]hydrazide (J147), and process for producing the crystalline polymorphic form are provided.

21 Claims, 17 Drawing Sheets

FIG 6

2,2,2-TRIFLUOROACETIC ACID 1-(2,4-DIMETHYLPHENYL)-2-[(3-METHOXYPHENYL)METHYLENE] HYDRAZIDE POLYMORPHS AND METHOD OF MAKING THE SAME

RELATED PATENT APPLICATIONS

This patent application claims the benefit of, and is a U.S. national phase of, International PCT Patent Application No. PCT/US2019/018835 filed Feb. 20, 2019, entitled 2,2,2-TRIFLUOROACETIC ACID 1-(2,4-DIMETHYLPHENYL)-2-[(3-METHOXYPHENYL) METHYLENE] HYDRAZIDE POLYMORPHS AND METHOD OF MAKING THE SAME; which claims the benefit of U.S. Provisional Patent Application No. 62/633,441 filed on Feb. 21, 2018, entitled 2,2,2-TRIFLUOROACETIC ACID 1-(2,4-DIMETHYLPHENYL)-2-[(3-METHOXYPHENYL)METHYLENE] HYDRAZIDE POLYMORPHS AND METHOD OF MAKING THE SAME. The entire content of the foregoing application is incorporated herein by reference, including all text, tables and drawings.

BACKGROUND

The present disclosure relates to polymorph forms of a pharmaceutical active agent. In particular, the present disclosure relates to polymorph forms of neuroprotective agent 2,2,2-trifluoroacetic acid 1-(2,4-Dimethylphenyl)-2-[(3-methoxyphenyl)methylene] hydrazide (J147).

2,2,2-trifluoroacetic acid 1-(2,4-Dimethylphenyl)-2-[(3-methoxyphenyl)methylene] hydrazide (J147) is a potent orally active neurotrophic agent discovered during screening for efficacy in cellular models of age-associated pathologies and has a structure given by Formula I:

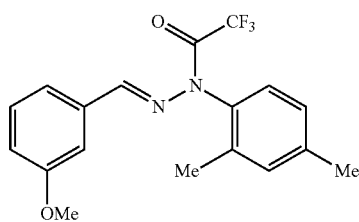

J147 is broadly neuroprotective, and exhibited activity in assays indicating distinct neurotoxicity pathways related to aging and neurodegenerative diseases, with $EC_{50}$ between 10 and 200 nM. It has been indicated to improve memory in normal rodents, and prevent the loss of synaptic proteins and cognitive decline in a transgenic AD mouse model. Furthermore, it has displayed neuroprotective, neuroanti-inflammatory, and LTP-enhancing activity.

The neurotrophic and nootropic effects have been associated with increases in BDNF levels and BDNF responsive proteins. Interestingly, despite this mechanism of action, J147's neuroprotective effects have been observed to be independent of TrkB receptor activation. J147 has been indicated to reduce soluble Aβ40 and Aβ42 levels, and it is currently being researched for potential applications in treating ALS.

SUMMARY

The present disclosure is directed to a crystalline Form II of 2,2,2-trifluoroacetic acid 1-(2,4-Dimethylphenyl)-2-[(3-methoxyphenyl)methylene]hydrazide (J147), and methods of making thereof.

Certain embodiments of the present disclosure provide a method of making crystalline Form II of 2,2,2-trifluoroacetic acid 1-(2,4-Dimethylphenyl)-2-[(3-methoxyphenyl)methylene] hydrazide (J147), having a powder X-ray diffraction pattern comprising peaks located at 13.37, 18.47, and 23.34+/−0.2 degrees 2-theta, the method comprising: providing a slurry comprising saturated amorphous or crystalline Form I of 2,2,2-trifluoroacetic acid 1-(2,4-Dimethylphenyl)-2-[(3-methoxyphenyl)methylene] hydrazide (J147) in a solvent/anti-solvent mixture; and mixing the slurry to provide crystalline Form II.

Certain embodiments of the present disclosure provide an isolated crystalline Form I of 2,2,2-trifluoroacetic acid 1-(2, 4-Dimethylphenyl)-2-[(3-methoxyphenyl)methylene]hydrazide (J147), having a powder X-ray diffraction pattern comprising peaks located at 11.85, 17.11, 17.79, and 23.40+/−0.2 degrees 2-theta.

BRIEF DESCRIPTION OF DRAWINGS

Various embodiments of the present disclosure will be described herein below with reference to the figures wherein:

FIG. 6 shows proton nuclear magnetic resonance (NMR) spectrum of crystalline Form I of J147.

DETAILED DESCRIPTION

Figure 1:
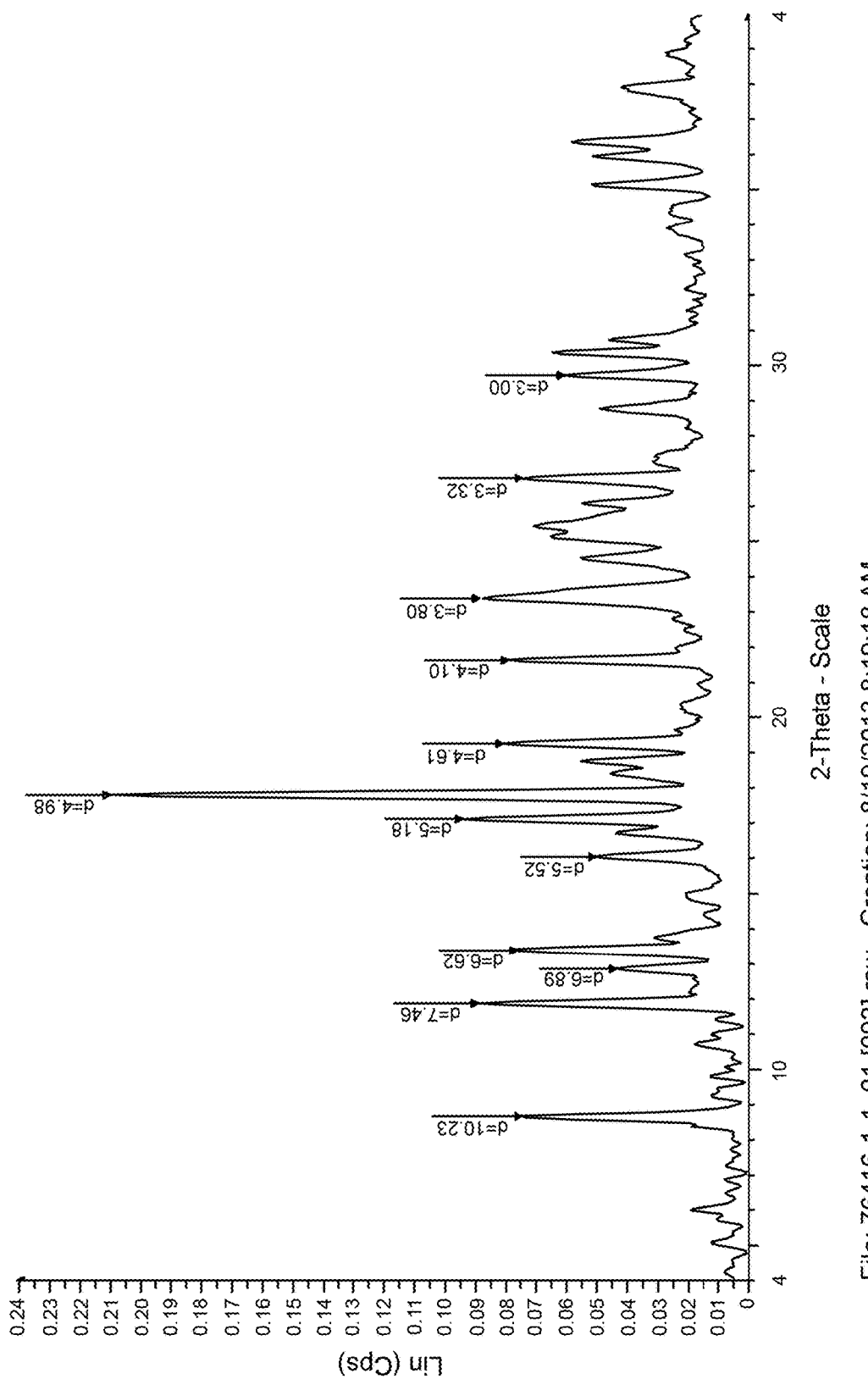
FIG. 1 shows the X-ray Diffraction (XRD) diffractogram of crystalline Form I of 2,2,2-trifluoroacetic acid 1-(2,4-Dimethylphenyl)-2-[(3-methoxyphenyl)methylene] hydrazide (J147).

Embodiments herein are directed to various polymorph forms of 2,2,2-trifluoroacetic acid 1-(2,4-Dimethylphenyl)-2-[(3-methoxyphenyl)methylene]hydrazide (J147) and methods of preparing such forms. Discovery of polymorph forms of active pharmaceutical ingredients is recognized as an important practice in product development. Polymorph forms of J147 disclosed herein may affect various physicochemical properties of J147 including, without limitation, hardness, stability, filterability, solubility, hygroscopicity, melting point, solid density and flowability. Altering one or more physicochemical properties of J147 may lead to downstream improvements in both manufacture as well as having an impact on pharmacokinetics and other aspects of administering the API.

In some embodiments, there is provided an isolated crystalline Form I of 2,2,2-trifluoroacetic acid 1-(2,4-Dimethylphenyl)-2-[(3-methoxyphenyl)methylene]hydrazide (J147), having a powder X-ray diffraction pattern comprising peaks located at 11.85, 17.11, 17.79, and 23.40+/−0.2 degrees 2-theta.

As used herein, "isolated" refers to the separation of a polymorph form, specifically of J147, to the substantial exclusion of other forms as well as impurities and, if so desired, solvent. For example, an isolated polymorph may have a purity of at least about 95%, or about 98%, or about 99%, or about 99.5%, including up to the limits of detection of impurities, or nominally 100% pure.

In some embodiments, isolated crystalline Form I may further comprise X-ray diffraction peaks located at 8.64, 13.36, 19.25, 21.64, and 26.81+/−0.2 degrees 2-theta.

In some embodiments, there is provided isolated crystalline Form II of 2,2,2-trifluoroacetic acid 1-(2,4-Dimethylphenyl)-2-[(3-methoxyphenyl)methylene]hydrazide (J147), having a powder X-ray diffraction pattern comprising peaks located at 13.37, 18.47, and 23.34+/−0.2 degrees 2-theta.

In some embodiments, isolated crystalline Form II may further comprise X-ray diffraction peaks located at 17.74, 20.39, 26.25, and 28.74+/−0.2 degrees 2-theta.

Other XRD minor peaks in the spectra of Form I and Form II may be present, as disclosed herein below in the Examples.

In some embodiments, there are provided methods of making crystalline Form I of 2,2,2-trifluoroacetic acid 1-(2,4-Dimethylphenyl)-2-[(3-methoxyphenyl)methylene]hydrazide (J147), having a powder X-ray diffraction pattern comprising peaks located at 11.85, 17.11, 17.79, and 23.40+/−0.2 degrees 2-theta, the method comprising recrystallizing 2,2,2-trifluoroacetic acid 1-(2,4-Dimethylphenyl)-2-[(3-methoxyphenyl)methylene]hydrazide from an organic solvent selected from the group consisting of nitromethane, methylethylketone, tetrahydrofuran, acetone, acetonitrile, heptane, isopropyl ether, isopropyl acetate, and chloroform.

In general, recrystallization techniques familiar to those skilled in the art apply in the practice of the methods disclosed herein. For example, a sample of J147 may be dissolved in a minimal amount solvent including dissolution at elevated temperatures for a given solvent. J147 has been found to be reasonably soluble across an array of solvent types, including polar protic and polar aprotic solvents. J147 generally has lower solubility in highly hydrophobic hydrocarbon solvents such as heptane, or at the opposite end, lower solubility in water. Thus, such solvents can serve as co-solvents or anti-solvents during recrystallization. Recrystallization may be performed with or without stirring, mixing, agitation, or the like.

In some embodiments, the methods of preparing Form I may further employ water as an anti-solvent. In some embodiments, a ratio of organic solvent to anti-solvent water is in a range from about 4:1 to about 1:4.

In accordance with the methods disclosed herein and as exemplified below, a yield of Form I is obtainable in some embodiments in a range from about 50% to about 100%, or about 90% to about 100%. In some embodiments, the yield may be at least about 95% based on the amount of J147 being recrystallized, or at least about 98%, or at least about 99%, or quantitative recovery.

In some embodiments, there are provided methods of making crystalline Form I of 2,2,2-trifluoroacetic acid 1-(2,4-Dimethylphenyl)-2[(3-methoxyphenyl)methylene]hydrazide (J147), having a powder X-ray diffraction pattern comprising peaks located at 11.85, 17.11, 17.79, and 23.40+/−0.2 degrees 2-theta, the method comprising recrystallizing 2,2,2-trifluoroacetic acid 1-(2,4-Dimethylphenyl)-2[(3-methoxyphenyl)methylene]hydrazide from a solvent-anti-solvent mixture comprising an alcohol as the solvent. In some such embodiments, a ratio of solvent to the anti-solvent is in a range from about 4:1 to about 1:4. In some embodiments, the solvent alcohol is a $C_1$-$C_4$ alcohol. Thus, for example, the alcohol may be selected from the group consisting of methanol, ethanol, 1-propanol, 2-propanol, trifluoroethanol, 1-butanol and 2-butanol. In some embodiments the anti-solvent is water or heptane.

In accordance with the methods disclosed herein and as exemplified below, a yield of Form I is obtainable in some embodiments in a range from about 50% to about 100%. In some embodiments, the yield may be at least about 95% based on the amount of J147 being recrystallized, or at least about 98%, or at least about 99%, or quantitative recovery.

In some embodiments, there are provided method of making crystalline Form II of 2,2,2-trifluoroacetic acid 1-(2,4-Dimethylphenyl)-2[(3-methoxyphenyl)methylene] hydrazide (J147), having a powder X-ray diffraction pattern comprising peaks located at 13.37, 18.47, and 23.34+/−0.2 degrees 2-theta, the method comprising providing a slurry comprising a saturated crystalline Form I of 2,2,2-trifluoroacetic acid 1-(2,4-Dimethylphenyl)-2-[(3-methoxyphenyl) methylene]hydrazide (J147) in a solvent/anti-solvent mixture comprising water as anti-solvent and mixing the slurry at ambient temperature to provide crystalline Form II.

As used herein, "mixing" is broadly intended to include mixing, stirring, agitation and the like.

In some embodiments, Form II can be accessed via amorphous J147.

In some embodiments, the methods to access Form II of J147 may employ a solvent which is selected from the group consisting of an alcohol, dimethylformamide (DMF), and dimethylacetamide (DMA).

In some embodiments, the methods to access Form II of J147 involve the use of a solvent alcohol which is selected from the group consisting of methanol, ethanol, trifluoroethanol, 1-propanol, and 2-propanol.

In some embodiments, the methods to access Form II of J147 a ratio of the solvent/anti-solvent mixture is in a range from about 1:2 to about 1:1.

In some embodiments, the methods to access Form II of J147 includes mixing the slurry of saturated J147 over several days such as about 6 days. In some embodiments, mixing may optionally be accompanied by heating. However, ambient laboratory conditions, i.e., about 25° C. are generally sufficient. In some embodiments, Form II may be accessible in reasonable purity and quantities after about 3 days, or about 4 days, or about 5 days. Naturally, Form II may also be isolated at intervals longer than 6 days if so desired, including about 7 days or about 8 days.

In some embodiments, methods for forming Form II from the slurry includes the use of an apparatus comprising a vessel connected to a re-circulation system. In some embodiments, the recirculation can be conducted through a homogenization apparatus in which a shear force is applied. The homogenization apparatus may comprise a stator and a rotatable rotor, and the high-shear mixing force is applied by rotating the rotor at a speed of more than 250 rpm. The rotor can also be rotated as speeds of more than 500 rpm and more than 1,000 rpm.

Re-circulating the slurry may comprise regulating the flow of slurry through the outlet and the inlet of the vessel. The energy for the re-circulation can be provided by a pump. Conventional flow regulation mechanisms such as metering pumps, valves, and the like may be used for this purpose. The process can also be conducted in a continuous mode.

In embodiments, Form I or amorphous J147 may be in a supersaturated solution dissolved in a solvent. This solution may be mixed with an anti-solvent solution. The anti-solvent refers to any solvent in which the chemical material has a poor solubility. It may be a mixture of anti-solvents and solvents. For example, the anti-solvent may comprise water or heptane. Mixing the solutions reduces the solubility of the material in the solvent mixture, causing it to crystallize out.

In embodiments, methods may also include the step of introducing seed crystals into the vessel to facilitate crystallization. The seed crystals may be placed into the supersaturated solution or into an anti-solvent. These seed crystals are selected to be insoluble in the individual solvents and in the solvent mixture.

Mixing may comprise regulating the flow of the solution into the vessel. Conventional flow regulation mechanisms such as metering pumps, valves, and the like may be used for this purpose.

The temperature may be adjusted prior to their introduction into the vessel. This may be achieved by any conventional temperature adjusting equipment, such as a heater or a cooling bath associated with the solution source.

In embodiments, the re-circulation system may comprise a homogenization apparatus; outlet means for transferring the slurry from the vessel to the homogenization apparatus; and inlet means for receiving the slurry from the homogenization apparatus into the vessel. The homogenization apparatus may comprise a stator and a rotatable rotor, and means for applying a high-shear mixing force by rotating the rotor. The high-shear mixing force can be applied by rotating the rotor at a speed of more than 250 rpm. The rotor can also be rotated as speeds of more than 500 rpm and more than 1,000 rpm.

The apparatus may include a means for regulating the flow of slurry through the homogenization apparatus. Conventional flow regulation mechanisms such as metering pumps, valves, and the like may be used for this purpose. The apparatus may also include a means for adjusting the temperature of the slurry in the vessel. This may be achieved by any conventional temperature adjusting equipment, such as a heater or a cooling bath associated with the solution source or the vessel.

In accordance with the methods disclosed herein and as exemplified below, in some embodiments, a yield of Form II is obtainable in a range from about 50% to about 100%, or about 90% to about 100%. In some embodiments, the yield may be at least about 95% based on the amount of J147 being recrystallized, or at least about 98%, or at least about 99%, or quantitative recovery.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

This example describes the screening of J147 for polymorphic behavior. The screen was performed using solvent recrystallization, hydration experiments, competitive and non-competitive slurry experiments, and grinding to manipulate the solid state form of the test material. Samples generated were characterized using differential scanning calorimetry (DSC), polarized light microscopy, thermogravimetric analysis (TGA), Fourier transform nuclear magnetic resonance (NMR) spectroscopy, powder X-ray diffraction (XRD), Fourier Transform Infrared spectroscopy (FTIR), Raman Spectroscopy and dynamic vapor sorption/desorption (DVS). The polymorph screen revealed that the J147 is polymorphic, and several solid state forms were identified and characterized. The thermodynamically stable form was identified.

Experimental Methods

Microscopy: A Zeiss Universal and/or Olympus BX53 microscope configured with a polarized visible light source and polarizable analyzer were used to evaluate the optical properties of the samples. The specimens were typically mounted on a microscope slide with a cover glass. Observations of particle/crystal size and shape and birefringence were recorded.

Hot Stage Microscopy (Hsm): A Linkam hot stage accessory was used in tandem with the microscope. The specimens were mounted on a microscope slide with a cover glass. The samples were heated from room temperature through melting using a Linkam TMS 94 temperature control and Linksys 32 data capture software system. Observations of possible phase change, melting, recrystallization, decomposition, etc. were recorded.

Proton Nuclear Magnetic Resonance Spectroscopy (1H-NMR): The samples were prepared by dissolving 1 to 10 mg of the API in deuterated chloroform with 0.05% (v/v) tetramethylsilane (TMS). The spectra were collected at ambient temperature on a Bruker 400 MHz NMR spectrometer.

Differential Scanning calorimetry (DSC): Differential Scanning calorimetry (DSC) is a technique used to measure characteristic heat flux of a test article as it is scanned through a temperature gradient under a controlled atmosphere. Thermal phase transitions such as endothermic melting and exothermic decomposition were recorded. The DSC data were collected on a TA Instruments DSC. In general, samples in the mass range of 1 to 10 mg were crimped in aluminum sample pans and scanned from 25 to approximately 150° C. at heating rates of 2, 10, 20, and 50° C./min using a nitrogen purge of 50 mL/min.

Thermogravimetric Analysis (TGA): Thermogravimetric Analysis involves the determination of the mass of a specimen as a function of temperature. The TGA data were collected on a TA Instruments Q500 TGA. In general, samples in the mass range of 2 to 10 mg were placed in an open, pre-tared platinum sample pan and attached by fine wire to a microbalance. The sample was suspended in a furnace, which was heated from 25 to about 250° C. at 10° C./min using a nitrogen purge at 100 mL/min. The sample weight change as a function of temperature was observed.

X-Ray Powder Diffraction (XRD): X-ray diffraction is an analytical technique used to study the crystalline nature of solid materials. X-rays incident on crystalline material are scattered in all directions. In certain directions, the scattered X-rays are constructively reinforced to form diffracted beams. The conditions for constructive diffraction are described by Bragg's Law and depend on the unique composition and spatial arrangements of the crystal structure. As such, each molecular solid diffracts X-rays in different directions and at different intensities resulting in a unique X-ray diffraction pattern. A variable temperature hot stage was used to manipulate sample temperature for some experiments.

The X-ray powder diffraction patterns were obtained using a Bruker D8 Discovery diffractometer equipped with an XYZ stage, laser video microscope for positioning, and a two-dimensional HiStar area Detector or a scintillation detector. A Cu K a radiation 1.5406 angstrom source operating at 40 kV and 40 mA was used to irradiate samples. The X-ray optics consists of a Gobel mirror coupled with a pinhole collimator of 0.5 mm Theta-theta continuous scans were employed with a sample-detector distance of approximately 30 cm, which gives an effective range of 4-40. The samples were mounted in low background quartz plates.

Hygroscopicity-Dynamic Vapor Sorption (DVS): DVS is a gravimetric screening technique that measures how quickly and how much of a solvent (water) is adsorbed by a sample. The relative humidity or vapor concentration surrounding the sample is varied while the change in mass of the sample is measured. A vapor sorption isotherm shows the equilibrium amount of vapor sorbed as a function of relativity humidity. The mass values at each relative humidity step are used to generate the isotherm. Isotherms are divided in two components: sorption for increasing humidity steps and desorption for decreasing humidity steps. A plot of kinetic data is also supplied which shows the change in mass and humidity as a function of time.

The samples were analyzed using a TA Q2000 automated dynamic vapor sorption analyzer. The samples were dried at 40° C. for 5 hours and then cooled to 25° C. with a dry nitrogen purge over them until they no longer lost mass at 0% RH. The samples were then subjected to 0 to 95% RH, back to 0% RH at 25° C. in 5% RH steps.

Fourier Transform Infrared Spectroscopy (FTIR): The Infrared spectra were obtained using a Nicolet 510 M-O Fourier transform infrared spectrometer, equipped with a Harrick Splitpea™ attenuated total reflectance device. The spectra were acquired from 4000 to 400 cm$^{-1}$ with a resolution of 4 cm$^{-1}$; 128 scans were collected for each analysis.

Raman Spectroscopy: The Raman spectra were obtained with a Thermo DXR dispersive Raman spectrometer using laser excitation at 780 nm. The spectra were acquired from 3300 to 100 cm$^{-1}$. The samples were analyzed as bulk powders.

Screening of J147 samples: Initial testing was performed by XRD, DSC, TGA, proton NMR, FTIR, and Raman spectrometry. X-ray powder diffraction was used to examine the material to determine if it was crystalline. FIG. 1 shows the XRD pattern of this material which was crystalline and designated as Form I. The corresponding peaks and their abundance are show in Table A below.

TABLE A

| Angle 2-Theta ° | d value Angstrom | Intensity Cps | Intensity % % |
|---|---|---|---|
| 8.64 | 10.23 | 0.07 | 35.4 |
| 11.85 | 7.46 | 0.09 | 42.2 |
| 12.84 | 6.89 | 0.04 | 20.4 |
| 13.36 | 6.62 | 0.08 | 36.2 |
| 16.04 | 5.52 | 0.05 | 23.8 |
| 17.11 | 5.18 | 0.09 | 44.7 |
| 17.79 | 4.98 | 0.21 | 100.0 |
| 19.25 | 4.61 | 0.08 | 38.4 |
| 21.64 | 4.10 | 0.08 | 37.6 |
| 23.40 | 3.80 | 0.09 | 42.0 |
| 26.81 | 3.32 | 0.07 | 35.3 |
| 29.76 | 3.00 | 0.06 | 28.7 |

Figure 2A:
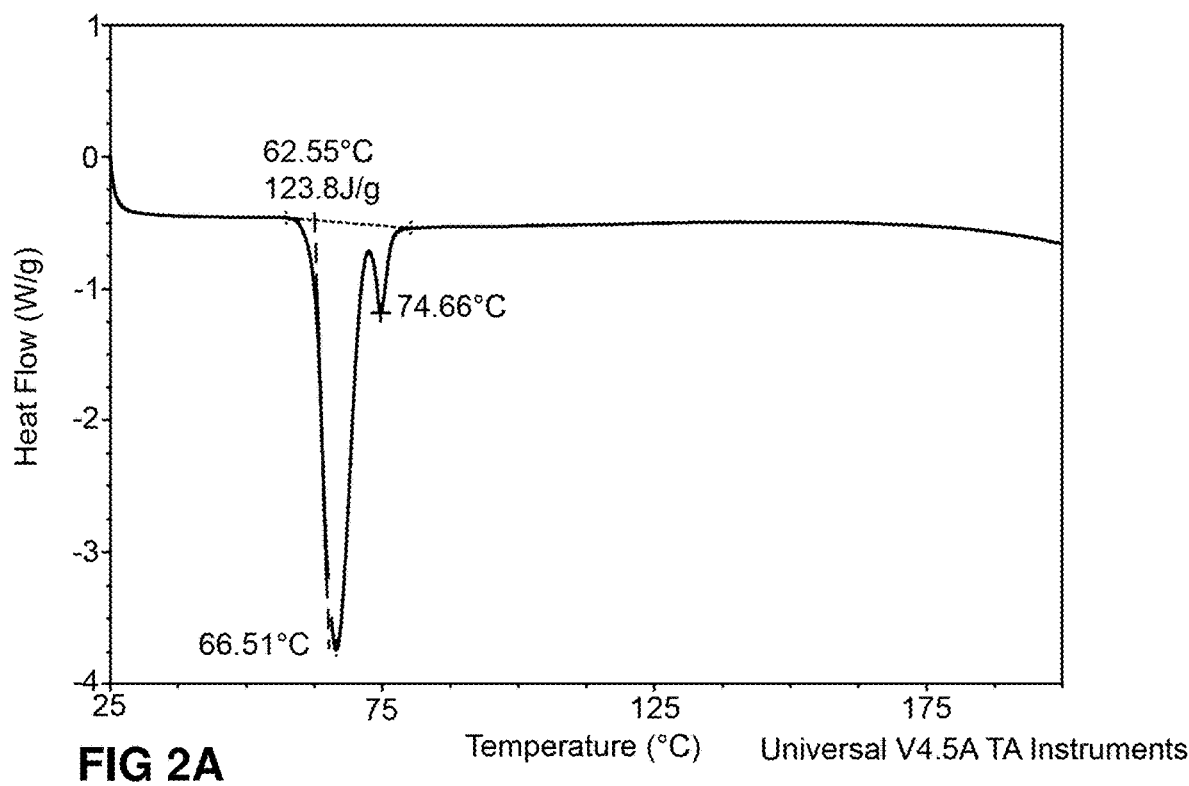
FIG. 2A shows a differential scanning calorimetry (DSC) thermogram of crystalline Form I of J147.
Figure 2B:
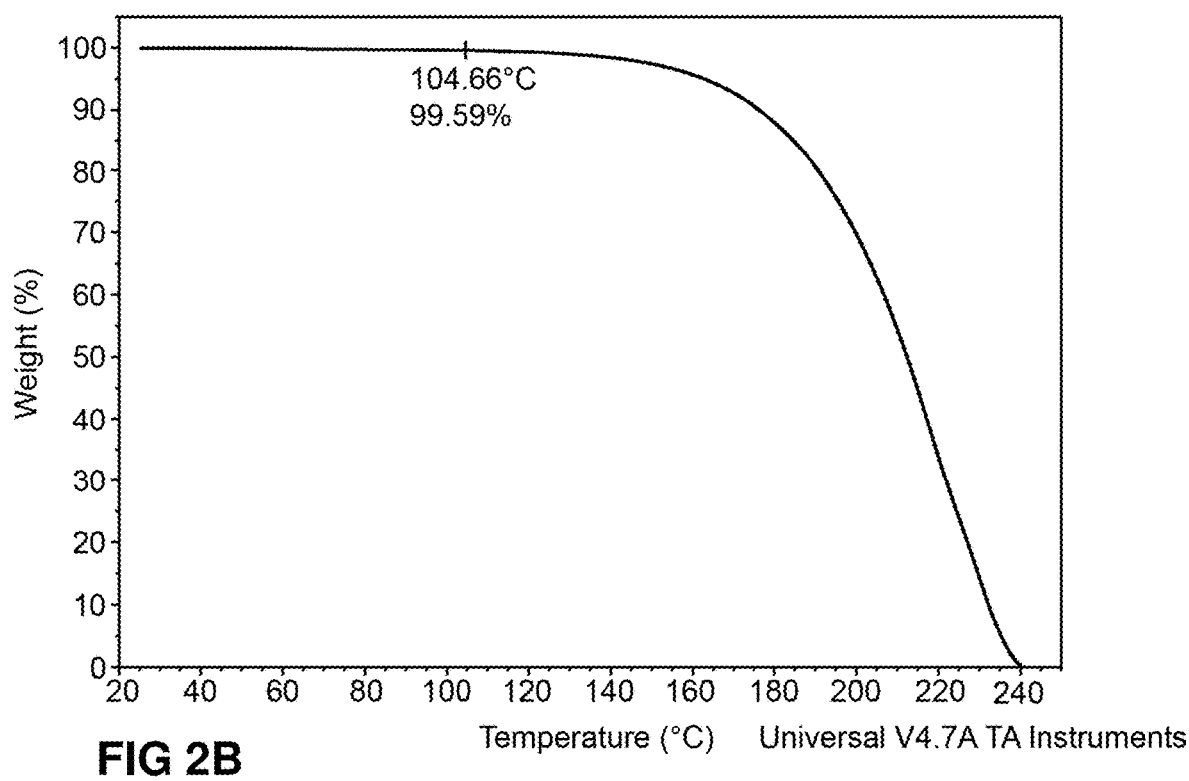
FIG. 2B shows a thermogravimetric (TGA) thermogram of crystalline Form I of J147.

The thermal behavior of Form I was determined by DSC and TGA. The DSC thermogram exhibited a melting endotherm with an onset of 62.6° C. The endotherm was split with peak maxima at 66.5° C. and 74.7° C. The heat of fusion was 123.8 J/g. This split endotherm proved to be due to a mixture of two polymorphic forms as observed by hot stage microscopy as described further below. The scanning TGA thermogram indicated the sample was free of volatiles with a weight loss of less than 0.4 weight % from 25° C. to 104.7° C. FIGS. 2A and 2B show the DSC and TGA thermograms, respectively.

Figure 3A:
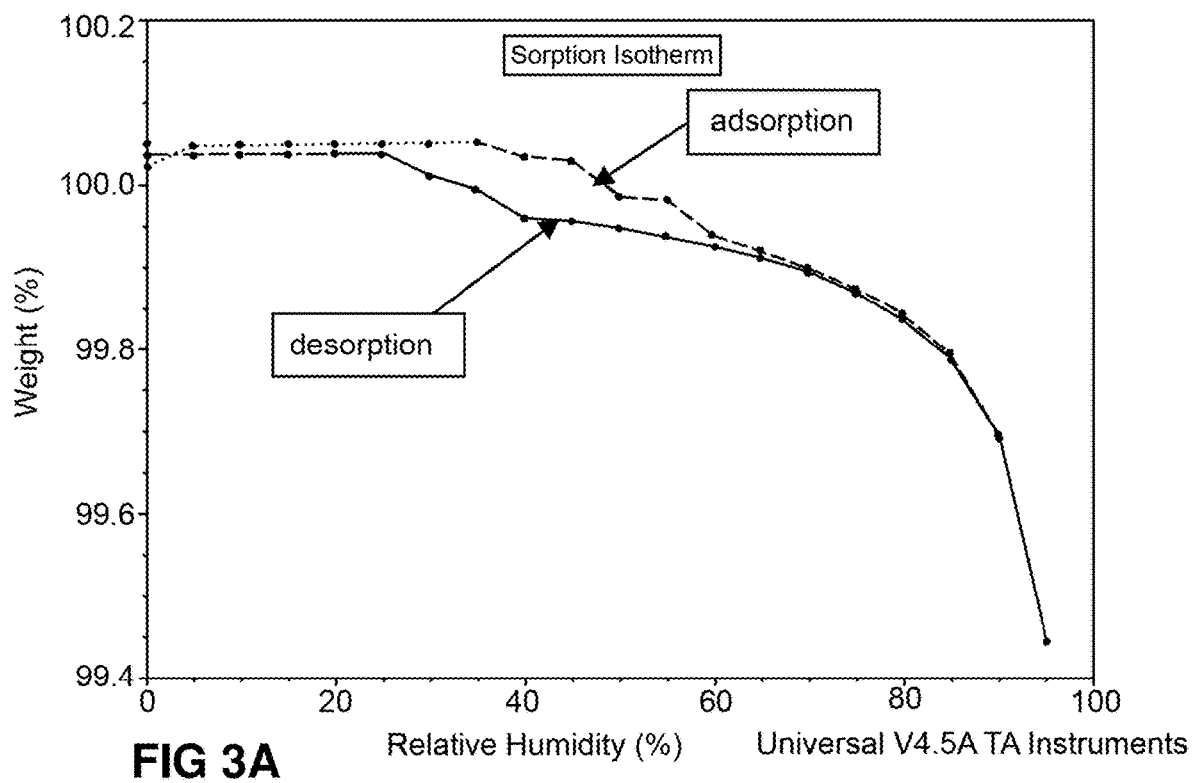
FIG. 3A shows dynamic vapor sorption isotherms of crystalline Form I of J147 using TGA.
Figure 3B:
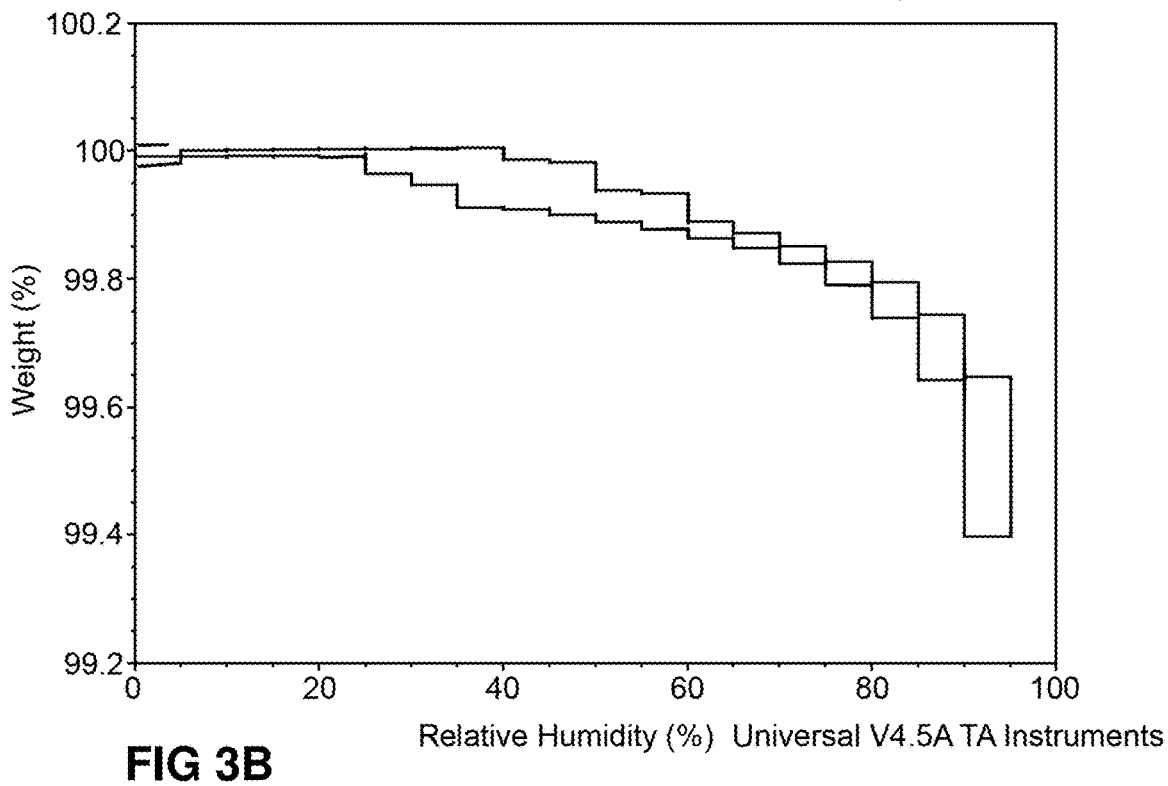
FIG. 3B shows kinetic plots of crystalline Form I of J147 using TGA.

Dynamic vapor sorption isotherms and the kinetic plots are shown in FIGS. 3A and 3B, respectively. The material proved very hydrophobic and did not appear to be prone to hydrate formation. A total weight loss of approximately 0.5% was observed at 95% RH. This unusual event (weight loss with high humidity) may be due to differences in the adsorption characteristics of the sample and reference pans and not the J147 sample.

Figure 4:
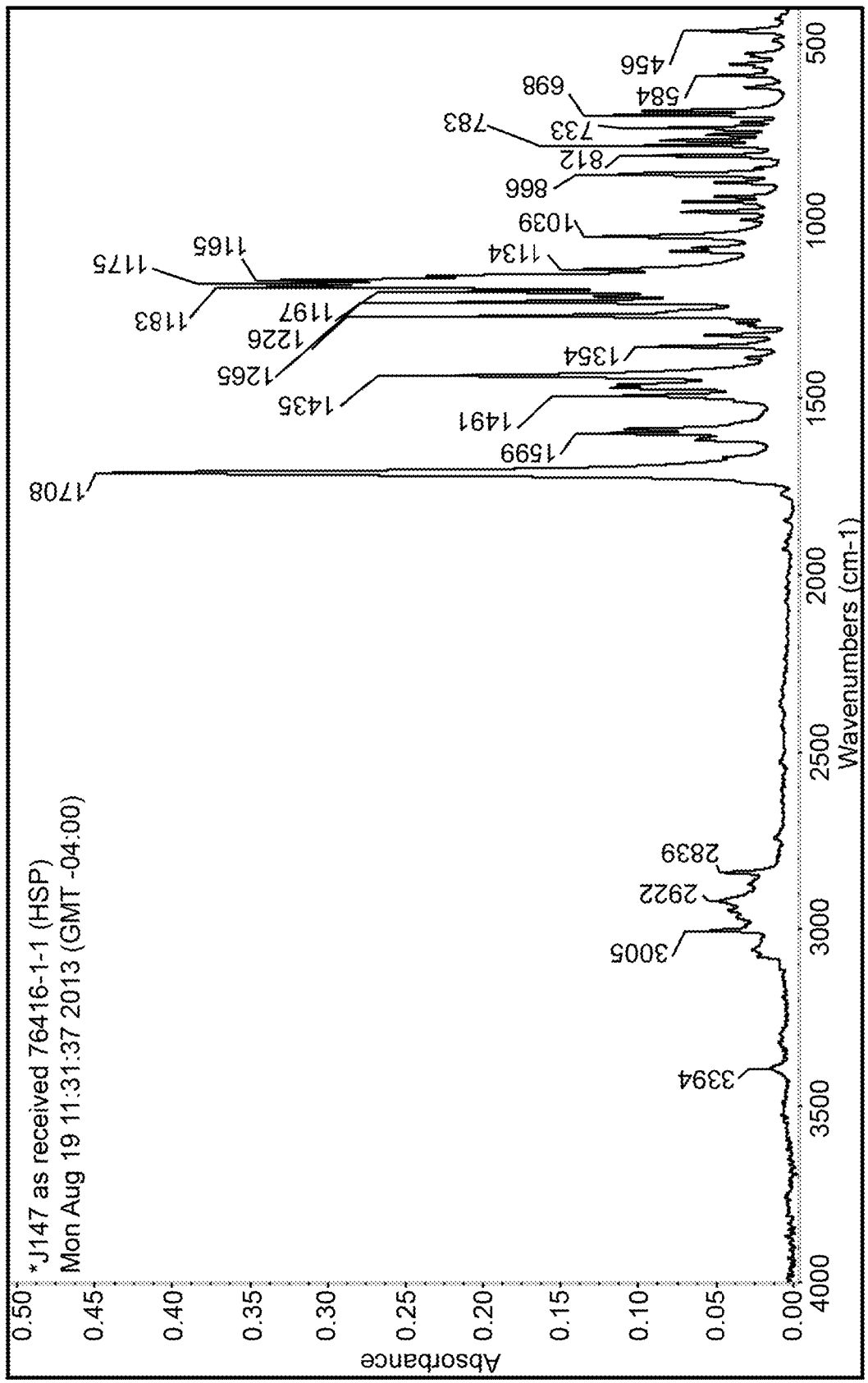
FIG. 4 shows the Fourier transform infrared (FTIR) spectrum of crystalline Form I of J147.
Figure 5:
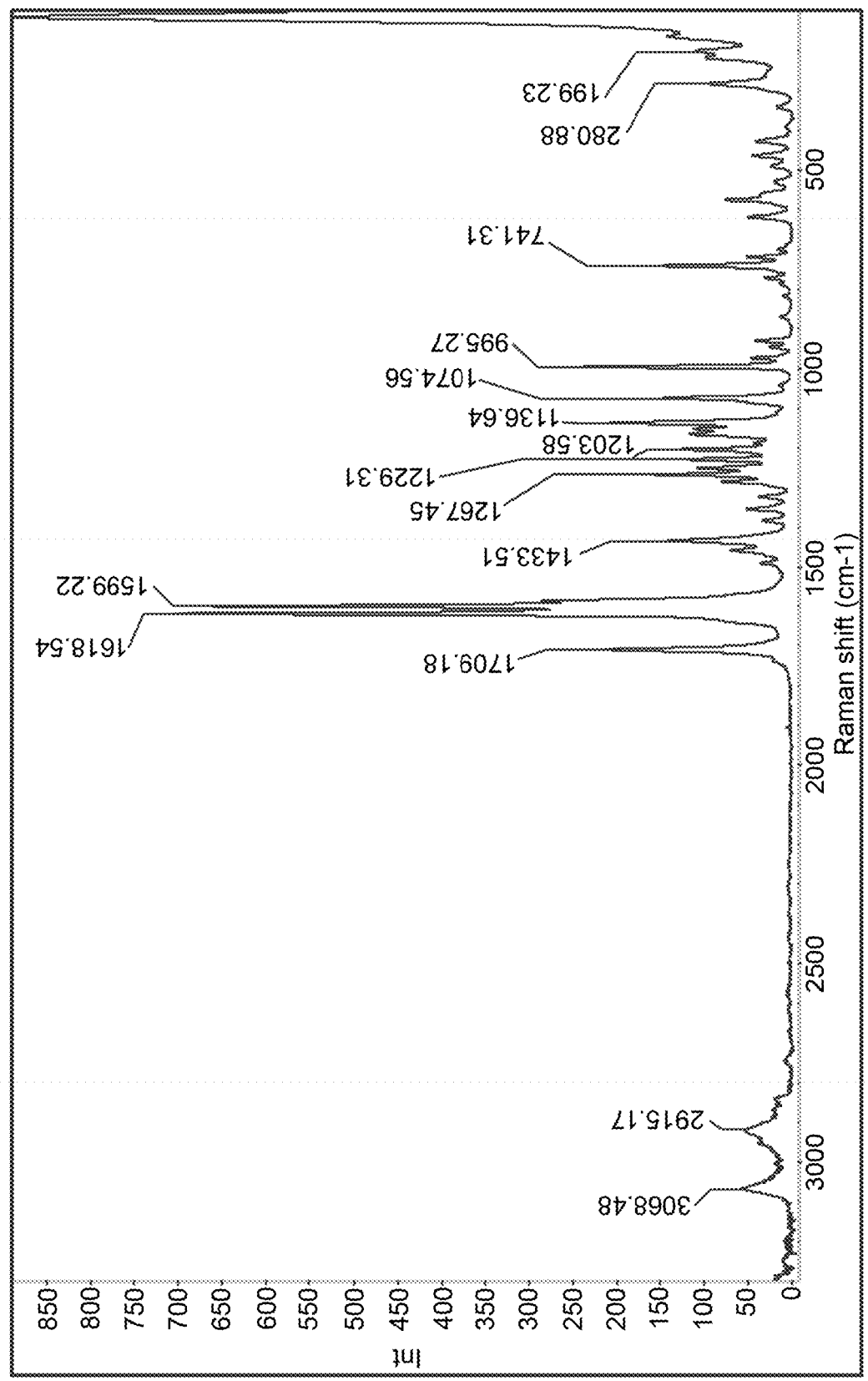
FIG. 5 shows the Raman spectrum of crystalline Form I of J147.
Figure 6:
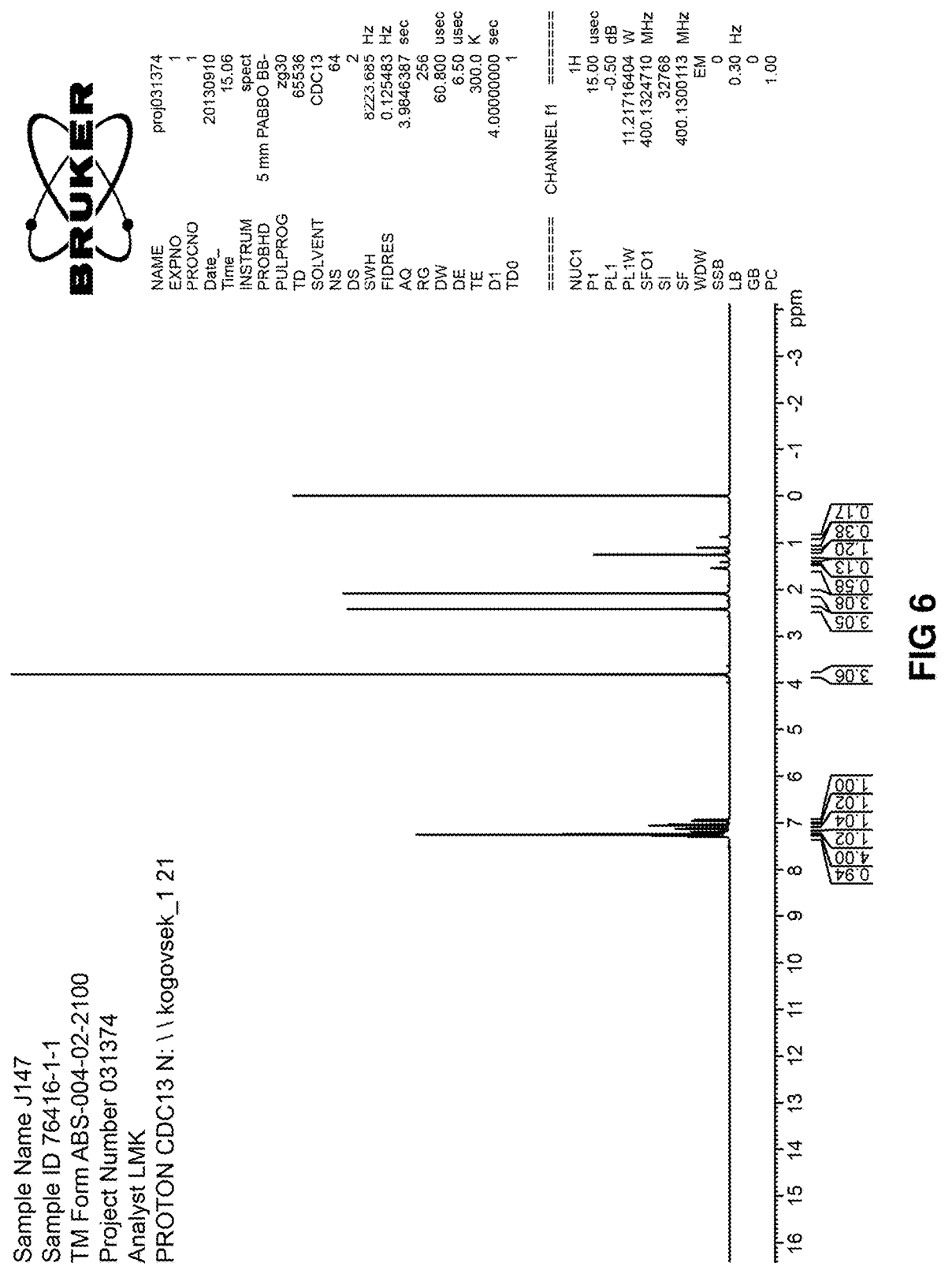

The Fourier transform infrared (FTIR) spectrum is shown in FIG. 4. Based on visual inspection the spectrum is consistent with structure. The Raman spectrum is in agreement with the FTIR spectrum and is shown in FIG. 5. The proton NMR data is consistent with the structure of J147 and is shown in FIG. 6. The proton NMR data is also shown in tabulated form in Table B below.

TABLE B

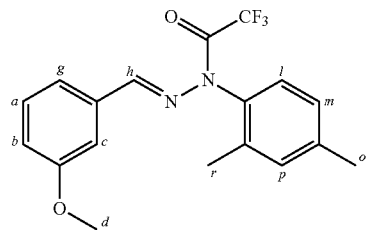 [SMILES: COc1cccc(/C=N/N(C(=O)C(F)(F)F)c2ccc(C)cc2C)c1]

| Chemical Shift (ppm) | Peak Type | Peak Area Integral | Tentative Proton Assignment |
|---|---|---|---|
| 7.298, 7.279 ~ 7.26 | doublet doublet | 4.94 | a |
| 7.256 | singlet | | chloroform |
| ~7.26 to ~ 7.23 | overlapping multiplets | | p, e, h |
| ~ 7.22 to ~ 7.19 | broad multiplet | 1.02 | m |
| 7.134 to 7.110 | multiplet | 1.04 | g |
| 7.059, 7.039 | doublet | 1.02 | l |
| 6.694 to 6.935 | doublet doublet doublet | 1.00 | b |
| 3.828 | singlet | 3.06 | d |
| 2.419 | singlet | 3.05 | o, r |
| 2.085 | singlet | 3.08 | |
| 1.547 | broad peak | 0.58 | water |
| 1.416 | broad peak | 0.13 | impurities |
| 1.255 | singlet | 1.20 | |
| 1.110 | broad peak | 0.38 | |
| 0897 to 0.862 | overlapping multiplets | 0.17 | |
| 0.000 | singlet | NA | TMS |

Polymorph Screening: The screen was performed using solvent-based recrystallization followed by X-ray diffraction analysis of the solids. Suspension slurry experiments and grinding were also employed to search for additional solid state forms.

Visual Solubility Measurement: Approximately 80 mg of J147 was placed into each of 25 vials. Solvent was added and vials were stirred for several minutes at ambient temperature, followed by visual observation for remaining solids. The solvent was incrementally added until the solids were dissolved, or until a maximum volume of solvent was added and the experiment was terminated. These stock solutions were used to set up further panels of experiments. J147 was found to be quite soluble in all solvents surveyed except for water. The visual solubility was determined and shown in Table 1.

TABLE 1

| Solvent | Approximate Solubility mg/mL |
|---|---|
| methanol | >80 |
| ethanol | >80 |
| trifluoroethanol | >80 |
| 1-propanol | >80 |
| 2-propanol | 40 |
| 1-butanol | 40 |
| 2-butanol | 40 |
| water | <1.6 |

TABLE 1-continued

| Solvent | Approximate Solubility mg/mL |
|---|---|
| dimethyl formamide (DMF) | >80 |
| dimethylacetamide (DMA) | >80 |
| butyl amine | >80 |
| pyridine | >80 |
| nitromethane | >80 |
| acetone | >80 |
| methyl ethyl ketone (MEK) | >80 |
| isopropyl ether | >80 |
| ethyl acetate | >80 |
| methyl tert butyl ether (MTBE) | >80 |
| isopropyl acetate | >80 |
| tetrahydrofuran (THF) | >80 |
| acetonitrile (ACN) | >80 |
| dichloromethane (DCM) | >80 |
| chloroform | >80 |
| toluene | >80 |
| heptane | 8.0 |

Solvent Recrystallization: To perform the solvent-based portion of the polymorph screen, the test material was recrystallized using various solvents under approximately 150 different crystal growth conditions. The scale of the recrystallization experiments was from approximately 6 mL to 15 ml. The crystal growth conditions were changed by using binary gradient arrays of solvent mixtures. Saturated solutions were prepared by agitating excess (as possible) test material in contact with the various solvent systems at the saturation temperature. If solids did not completely dissolve in the solvent, the mother liquor was separated from the residual solids by filtration. The mother liquor was then heated above the saturation temperature (overheated) to dissolve any remaining solids. The temperature of each solution was then adjusted to the growth temperature and a controlled nitrogen shear flow was introduced to begin solvent evaporation. Due to the high solubility of J147 in the majority of solvents, an ambient growth temperature was used in all experiments. The recrystallization conditions for the six solvent based panels used are summarized in Table 2. Each recrystallization panel contained from 15 to 27 wells. The wells within each panel contained different solvent compositions. Because of the different solvent composition in each well, each well acted as a different crystal growth experiment. Based on the XRD analysis carried out, a new polymorph of J147 was discovered. The first polymorph was designated as Form I while the second polymorph was designated as Form II. Table 2 summarizes the recrystallization panels for solvent-based polymorph screening. The compositional solvent matrices for the six recrystallization panels used during the solvent-based portion of the polymorph screen are shown in Tables 3 to 8.

TABLE 2

| Panel | No. of Wells | Scale (mL) | Solvent | Saturation Temp. (° C.) | Overheat Temp. (° C.) | Growth Temp. (° C.) | N₂ Flow Rate (psi) |
|---|---|---|---|---|---|---|---|
| 1 | 25 | 15 | Single | 25 | 40 | 25 | 1 |
| 2 | 27 | 15 | Binary | 25 | 40 | 25 | 1 |
| 4 | 27 | 6 | Binary | 25 | 40 | 25 | 1 |
| 5 | 27 | 6 | Binary | 25 | 40 | 25 | 1 |
| 6 | 15 | 6 | Binary | 25 | 40 | 25 | 1 |

TABLE 3

| Well | Solvent | XRD Form | Appearance |
|---|---|---|---|
| 1 | methanol | amorphous | orange glass |
| 2 | ethanol | amorphous | clear glass |
| 3 | trifluoroethanol | amorphous | clear glass |
| 4 | 1-propanol | amorphous | clear glass |
| 5 | 2-propanol | amorphous | clear glass |
| 6 | 1-butanol | amorphous | clear glass |
| 7 | 2-butanol | no sample | no sample |
| 8 | water | no sample | no sample |
| 9 | dimethyl formamide (DMF) | amorphous | clear glass |
| 10 | dimethylacetamide (DMA) | amorphous | clear glass |
| 11 | butyl amine | amorphous | orange glass |
| 12 | pyridine | amorphous | clear glass |
| 13 | nitromethane | I | yellow solid |
| 14 | acetone | amorphous | clear glass |
| 15 | methyl ethyl ketone (MEK) | I | yellow solid |
| 16 | isopropyl ether | amorphous | clear glass |
| 17 | ethyl acetate | amorphous | clear glass |
| 18 | methyl tert butyl ether (MTBE) | amorphous | clear glass |
| 19 | isopropyl acetate | amorphous | clear glass |
| 20 | tetrahydrofuran (THF) | I | white solid |
| 21 | acetonitrile (ACN) | amorphous | clear glass |
| 22 | dichloromethane (DCM) | amorphous | clear glass |
| 23 | chloroform | I | white solid |
| 24 | toluene | amorphous | clear glass |
| 25 | heptane | amorphous | clear glass |

TABLE 4

Solvent Matrix and XRD Result for Recrystallization Panel 2

| Solvent | Sample ID | Ratio of Solvents 1 | 2 | 3 | Co/Anti-Solvent |
|---|---|---|---|---|---|
| methanol | A | 12:3 | 7.5:7.5 | 3:12 | water |
| ethanol | B | 12:3 | 7.5:7.5 | 3:12 | water |
| trifluoroethanol | C | 12:3 | 7.5:7.5 | 3:12 | water |
| 1-propanol | D | 12:3 | 7.5:7.5 | 3:12 | water |
| 2-propanol | E | 12:3 | 7.5:7.5 | 3:12 | water |
| 1-butanol | F | 12:3 | 7.5:7.5 | 3:12 | water |
| 2-butanol | G | 12:3 | 7.5:7.5 | 3:12 | water |
| DMF | H | 12:3 | 7.5:7.5 | 3:12 | water |
| DMA | I | 12:3 | 7.5:7.5 | 3:12 | water |

| Solvent | Sample ID | XRD Form 1 | 2 | 3 | Co/Anti-Solvent |
|---|---|---|---|---|---|
| methanol | A | I | amorphous | I | water |
| ethanol | B | I | I | I | water |
| trifluoroethanol | C | amorphous | I | I | water |
| 1-propanol | D | I | amorphous | I | water |
| 2-propanol | E | amorphous | I | I | water |
| 1-butanol | F | amorphous | amorphous | amorphous | water |
| 2-butanol | G | amorphous | I | amorphous | water |
| DMF | H | amorphous | amorphous | amorphous | water |
| DMA | I | amorphous | amorphous | amorphous | water |

TABLE 5

Solvent Matrix and XRD Result for Recrystallization Panel 3

| Solvent | Sample ID | Ratio of Solvents 1 | 2 | 3 | Co/Anti-Solvent |
|---|---|---|---|---|---|
| butyl amine | A | 12:3 | 7.5:7.5 | 3:12 | water |
| pyridine | B | 12:3 | 7.5:7.5 | 3:12 | water |
| nitromethane | C | 12:3 | 7.5:7.5 | 3:12 | water |
| acetone | D | 12:3 | 7.5:7.5 | 3:12 | water |

TABLE 5-continued

Solvent Matrix and XRD Result for Recrystallization Panel 3

| | | | | | |
|---|---|---|---|---|---|
| isopropyl acetate | E | 12:3 | 7.5:75 | 3:12 | water |
| THF | F | 12:3 | 7.5:7.5 | 3:12 | water |
| ACN | G | 12:3 | 7.5:7.5 | 3:12 | water |
| heptane | H | 12:3 | 7.5:7.5 | 3:12 | water |
| isopropyl ether | I | 12:3 | 7.5:7.5 | 3:12 | water |

| | | XRD Form | | | |
|---|---|---|---|---|---|
| Solvent | Sample ID | 1 | 2 | 3 | Co/Anti-Solvent |
| butyl amine | A | amorphous | amorphous | amorphous | water |
| pyridine | B | amorphous | amorphous | amorphous | water |
| nitromethane | C | amorphous | amorphous | I | water |
| acetone | D | I | amorphous | amorphous | water |
| isopropyl acetate | E | amorphous | amorphous | I | water |
| THF | F | amorphous | amorphous | I | water |
| ACN | G | amorphous | amorphous | I | water |
| heptane | H | I | I | amorphous | water |
| isopropyl ether | I | I | amorphous | amorphous | water |

TABLE 6

Solvent Matrix and XRD Result for Recrystallization Panel 4

| | | Ratio of Solvents | | | |
|---|---|---|---|---|---|
| Solvent | Sample ID | 1 | 2 | 3 | Co/Anti-Solvent |
| methanol | A | 12:3 | 7.5:7.5 | 3:12 | heptane |
| ethanol | B | 12:3 | 7.5:7.5 | 3:12 | heptane |
| trifluoroethanol | C | 12:3 | 7.5:7.5 | 3:12 | heptane |
| 1-propanol | D | 12:3 | 75:7.5 | 3:12 | heptane |
| 2-propanol | E | 12:3 | 7.5:7.5 | 3:12 | heptane |
| 1-butanol | F | 12:3 | 7.5:7.5 | 3:12 | heptane |
| 2-butanol | G | 12:3 | 7.5:7.5 | 3:12 | heptane |
| DMF | H | 12:3 | 7.5:7.5 | 3:12 | heptane |
| DMA | I | 12:3 | 7.5:7.5 | 3:12 | heptane |

| | | XRD Form | | | |
|---|---|---|---|---|---|
| Solvent | Sample ID | 1 | 2 | 3 | Co/Anti-Solvent |
| methanol | A | amorphous | amorphous | amorphous | heptane |
| ethanol | B | amorphous | amorphous | amorphous | heptane |
| trifluoroethanol | C | amorphous | I | amorphous | heptane |
| 1-propanol | D | amorphous | amorphous | amorphous | heptane |
| 2-propanol | E | amorphous | amorphous | amorphous | heptane |
| 1-butanol | F | amorphous | amorphous | not enough material | heptane |
| 2-butanol | G | I | I | not enough material | heptane |
| DMF | H | amorphous | not enough material | amorphous | heptane |
| DMA | I | amorphous | amorphous | amorphous | heptane |

TABLE 7

Solvent Matrix and XRD Result for Recrystallization Panel 5

| | | Ratio of Solvents | | | |
|---|---|---|---|---|---|
| Solvent | Sample ID | 1 | 2 | 3 | Co/Anti-Solvent |
| butyl amine | A | 12:3 | 7.5:7.5 | 3:12 | heptane |
| pyridine | B | 12:3 | 7.5:7.5 | 3:12 | heptane |
| nitromethane | C | 12:3 | 7.5:7.5 | 3:12 | heptane |
| acetone | D | 12:3 | 7.5:7.5 | 3:12 | heptane |
| MEK | E | 12:3 | 7.5:7.5 | 3:12 | heptane |
| isopropyl ether | F | 12:3 | 75:7.5 | 3:12 | heptane |

TABLE 7-continued

Solvent Matrix and XRD Result for Recrystallization Panel 5

| | | | | | |
|---|---|---|---|---|---|
| ethyl acetate | G | 12:3 | 7.5:7.5 | 3:12 | heptane |
| MTBE | H | 12:3 | 7.5:7.5 | 3:12 | heptane |
| isopropyl acetate | I | 12:3 | 7.5:7.5 | 3:12 | heptane |

| | | XRD Form | | | |
|---|---|---|---|---|---|
| Solvent | Sample ID | 1 | 2 | 3 | Co/Anti-Solvent |
| butyl amine | A | amorphous | amorphous | amorphous | heptane |
| pyridine | B | amorphous | amorphous | not enough material | heptane |
| nitromethane | C | amorphous | amorphous | not enough material | heptane |
| acetone | D | amorphous | amorphous | amorphous | heptane |
| MEK | E | amorphous | amorphous | amorphous | heptane |
| isopropyl ether | F | amorphous | amorphous | amorphous | heptane |
| ethyl acetate | G | amorphous | amorphous | amorphous | heptane |
| MTBE | H | not enough material | amorphous | amorphous | heptane |
| isopropyl acetate | I | amorphous | amorphous | amorphous | heptane |

TABLE 8

Solvent Matrix and XRD Result for Recrystallization Panel 6

| | | Ratio of Solvents | | | |
|---|---|---|---|---|---|
| Solvent | Sample ID | 1 | 2 | 3 | Co/Anti-Solvent |
| THF | A | 12:3 | 7.5:7.5 | 3:12 | heptane |
| ACN | B | 12:3 | 7.5:7.5 | 3:12 | heptane |
| DCM | C | 12:3 | 7.5:7.5 | 3:12 | heptane |
| chloroform | D | 12:3 | 7.5:7.5 | 3:12 | heptane |
| toluene | E | 12:3 | 7.5:7.5 | 3:12 | heptane |

| | | XRD Form | | | |
|---|---|---|---|---|---|
| Solvent | Sample ID | 1 | 2 | 3 | Co/Anti-Solvent |
| THF | A | amorphous | amorphous | amorphous | heptane |
| ACN | B | amorphous | amorphous | amorphous | heptane |
| DCM | C | amorphous | not enough material | amorphous | heptane |
| chloroform | D | not enough material | amorphous | amorphous | heptane |
| toluene | E | amorphous | amorphous | amorphous | heptane |

Non-Competitive Slurry Experiments: In addition to the solvent recrystallization experiments, non-competitive slurry experiments were performed to search for new solid state forms. These experiments rely on solubility differences of different polymorphic forms (if the compound exists in different polymorphic forms). As such, only polymorphs having a lower solubility (that is, are more stable) than the original crystalline form can result from a noncompetitive slurry experiment.

When a solid was mixed with solvent to create slurry, a saturated solution eventually resulted. The solution was saturated with respect to the polymorphic form dissolved. However, the solution was supersaturated with respect to any polymorphic form that is more stable (more stable forms have lower solubility) than the polymorphic form initially dissolved. Therefore, any of the more stable polymorphic forms can nucleate and precipitate from solution. In addition, noncompetitive slurry experiments are often useful in identifying solvents that form solvates with the compound.

The slurry experiments were performed by exposing excess supplied material to solvents and agitating the resulting suspensions for several days at ambient temperature. The solids were filtered (Whatman Grade 1, 11 μm pore size) and analyzed by XRD to determine the resulting form(s). To avoid possible desolvation or physical change after isolation, the samples were not dried before X-ray analysis. A summary of non-competitive slurry experiments is shown in Table 9.

TABLE 9

| Vehicle | Initial Form | Duration | Final Form |
|---|---|---|---|
| Methanol/water (1:1) | I | 6 days | II |
| Ethanol/water (1:1) | I | 6 days | II |
| Trifluoroethanol/water (1:1) | I | 6 days | II |
| 1-propanol/water (1:1) | I | 6 days | II |
| 2-proponal/water (1:1) | I | 6 days | II |
| DMF/water (1:1) | I | 6 days | II |
| DMA/water (1:1) | I | 6 days | II |

Based on their X-ray scattering behavior, all of the slurry experiments of Form I resulted in Form II after 6 days of slurring. These data indicate that Form II is more stable than Form I at ambient temperature and pressure. No new polymorphs, solvates, or hydrates were isolated in these experiments.

Figure 7:
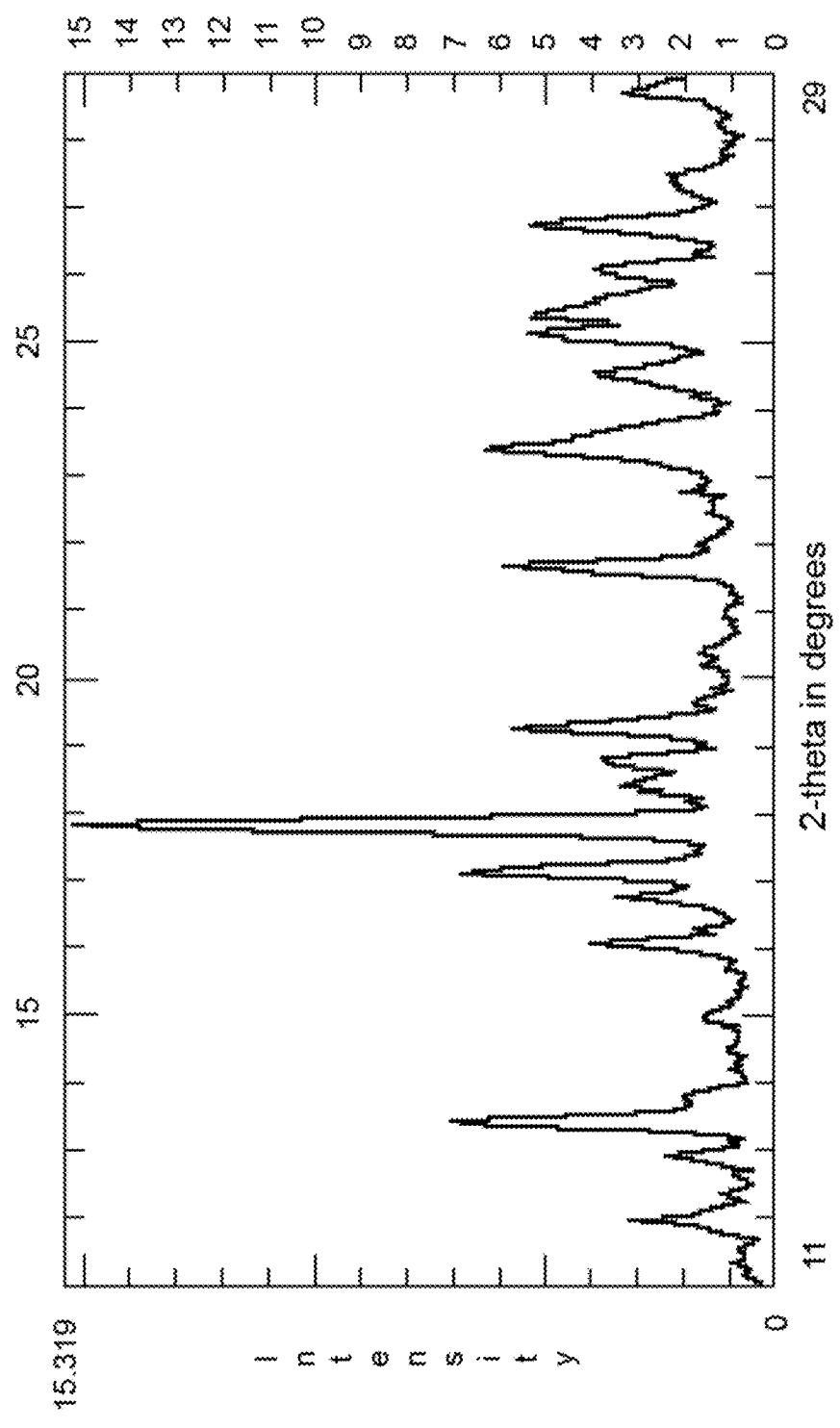
FIG. 7 shows graphical output using Debye cone integration using a two dimensional detector during XRD analysis of a sample of J147.

Solids generated from the solvent based recrystallization panels and synthesized were analyzed by powder XRD. To mitigate preferred grain effects, a two dimensional detection system was used to collect all the XRD screening data. The two dimensional detector integrates along the concentric Debye cones which helps reduce pattern variation. An example of the Debye cone integration using a two dimensional detector is shown in FIG. 7. If bright spots appear in the conical rings, it indicates strong preferred grain effects that can lead to considerable variability in the observed diffraction patterns including changes in peak intensities. Some samples of J147 exhibited preferred grain effects based on the appearance of the scattering behavior.

Figure 8:
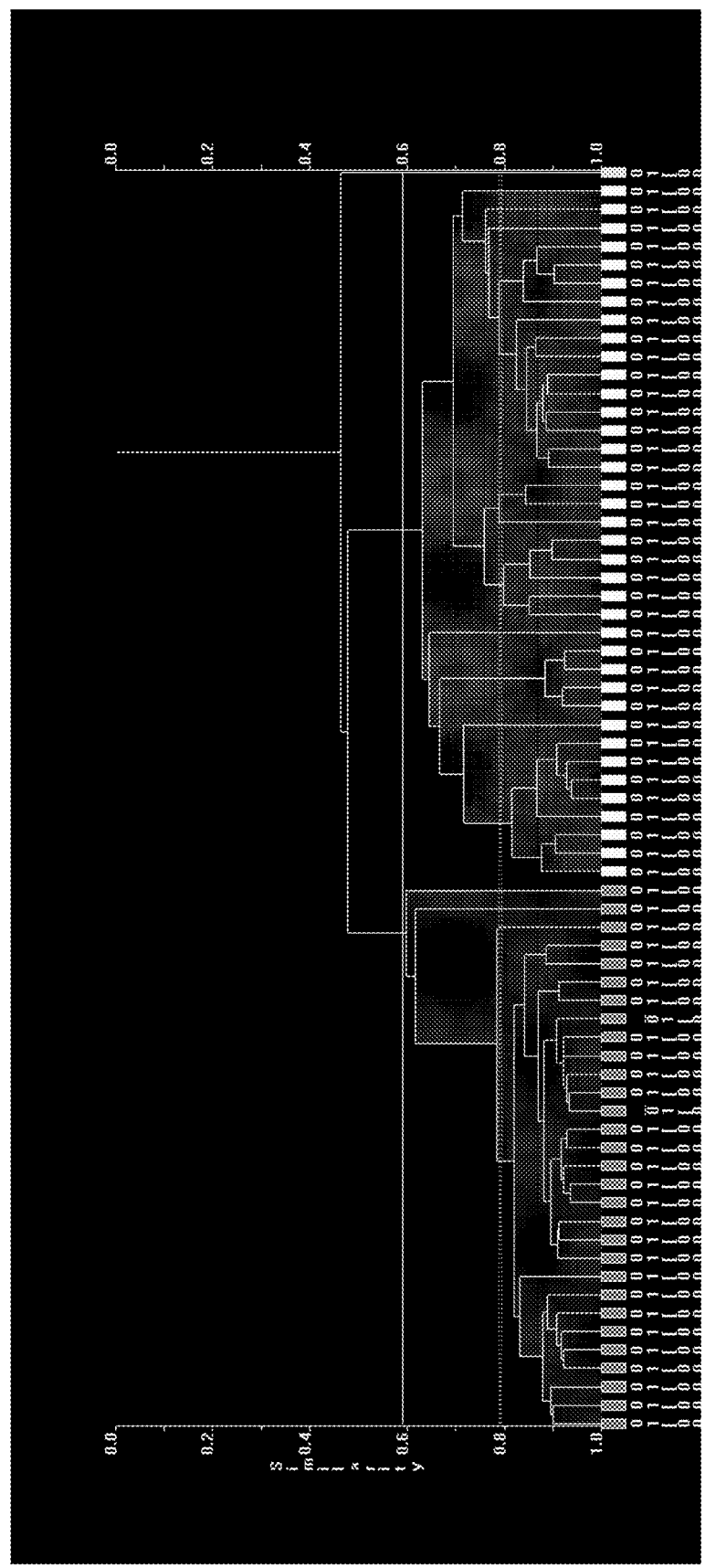
FIG. 8 shows a dendrogram of all XRD results in screening samples of J147.
Figure 9:
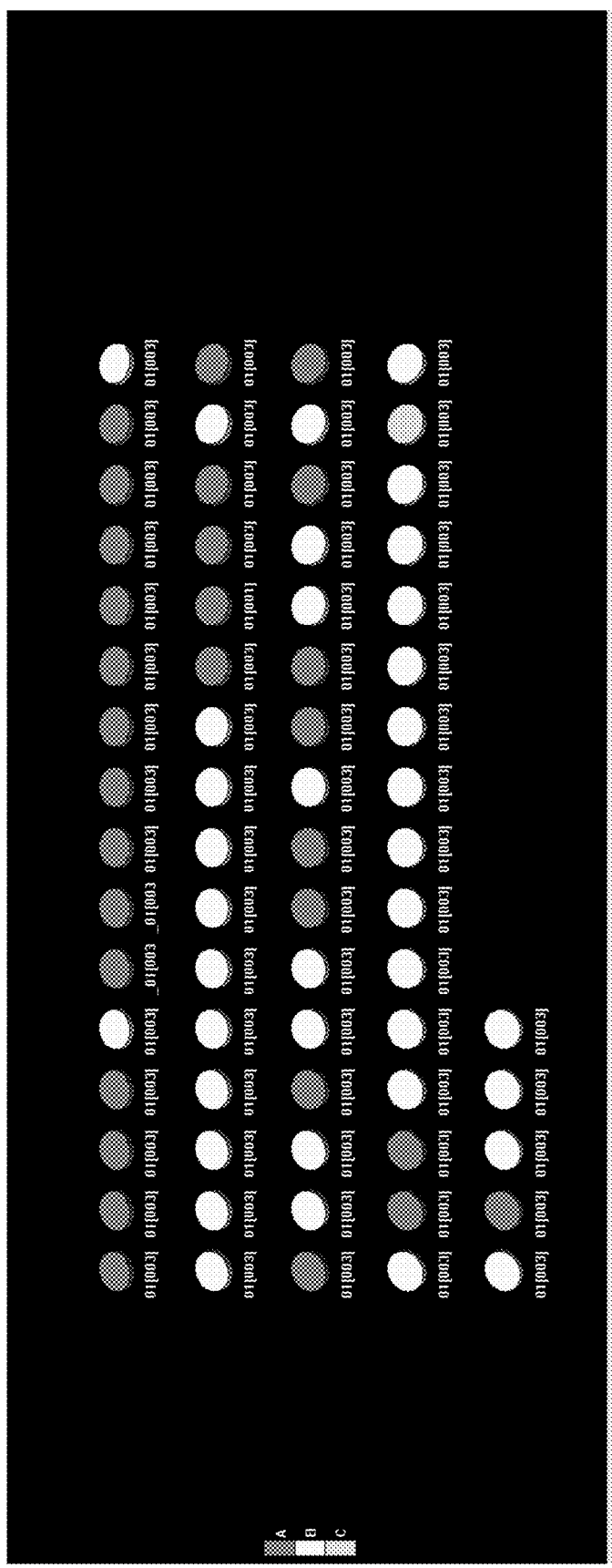
FIG. 9 shows a cell plot of all XRD results in screening samples of J147.
Figure 10:
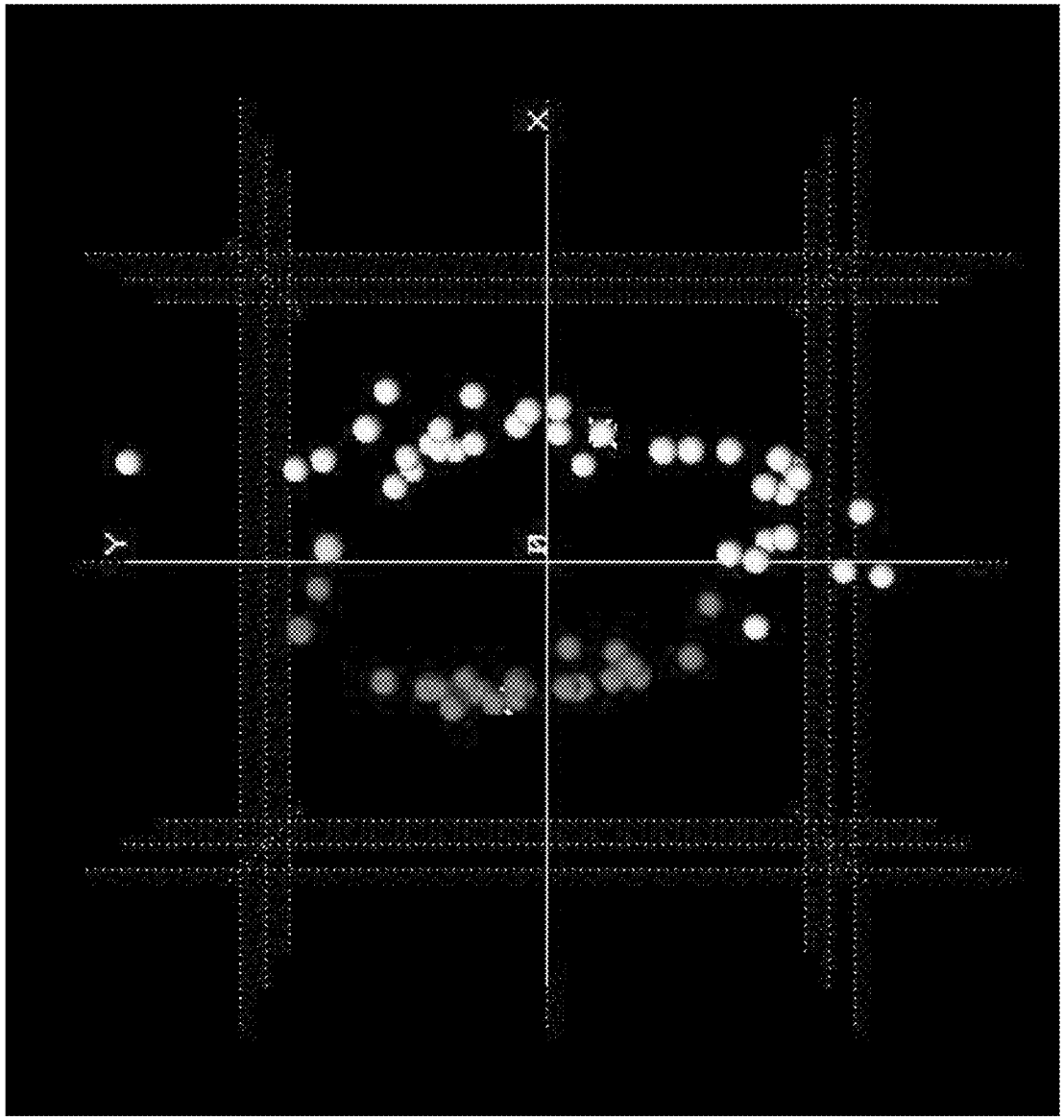
FIG. 10 shows a cluster plot of all XRD results in screening samples of J147.

The results of this analysis revealed the material exists as two different polymorphs. The polymorphs were designated as Forms I and II. The initially supplied material was designated as Form I. The resulting form designation for each individual (solvent-based) recrystallization experiment is shown in Tables 3 through 8 above. The XRD data collected during the study was evaluated using a full profile chemometric treatment to determine if the crystalline form of the samples had changed during the experiment. To simplify the assessment, X-ray amorphous samples were not included in the chemometric treatment. The analysis entailed cluster analysis and multivariate statistics to group together any patterns that were determined to be statistically the same. The results of this analysis are summarized in the dendrogram in FIG. 8, cell plot in FIG. 9, and cluster plot in FIG. 10. These figures provide a pictorial cluster analysis of product similarity.

The chemometric analysis of the diffraction data categorized the samples into 3 different groups (or clusters) labeled A through C. A summary showing the number of members in each group (A through C) is shown in Table 10.

TABLE 10

| Group | Designated Form | Members |
|---|---|---|
| A | II | 30 |
| B | I | 38 |
| C | Low crystallinity, no form identified | 1 |

The characteristics of each group/form are summarized as follows. After classifying the data into different forms based on diffraction behavior, each form was studied to determine if other properties of the forms could be differentiated. The characterization of each form began by comparing the diffraction data representative of each form with that from the other forms. This was generally followed by DSC, TGA, DVS analysis and microscopy.

Figure 11A:
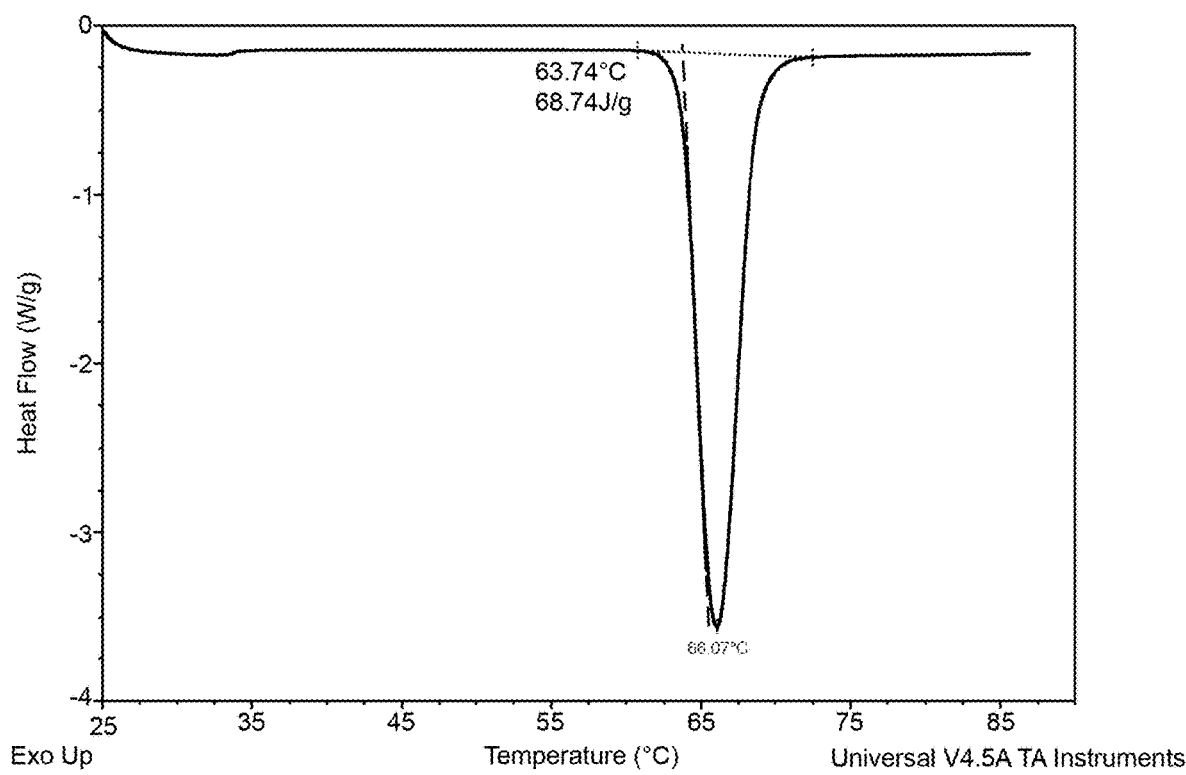
FIG. 11A shows a DSC thermogram of crystalline Form I of J147.
Figure 11B:
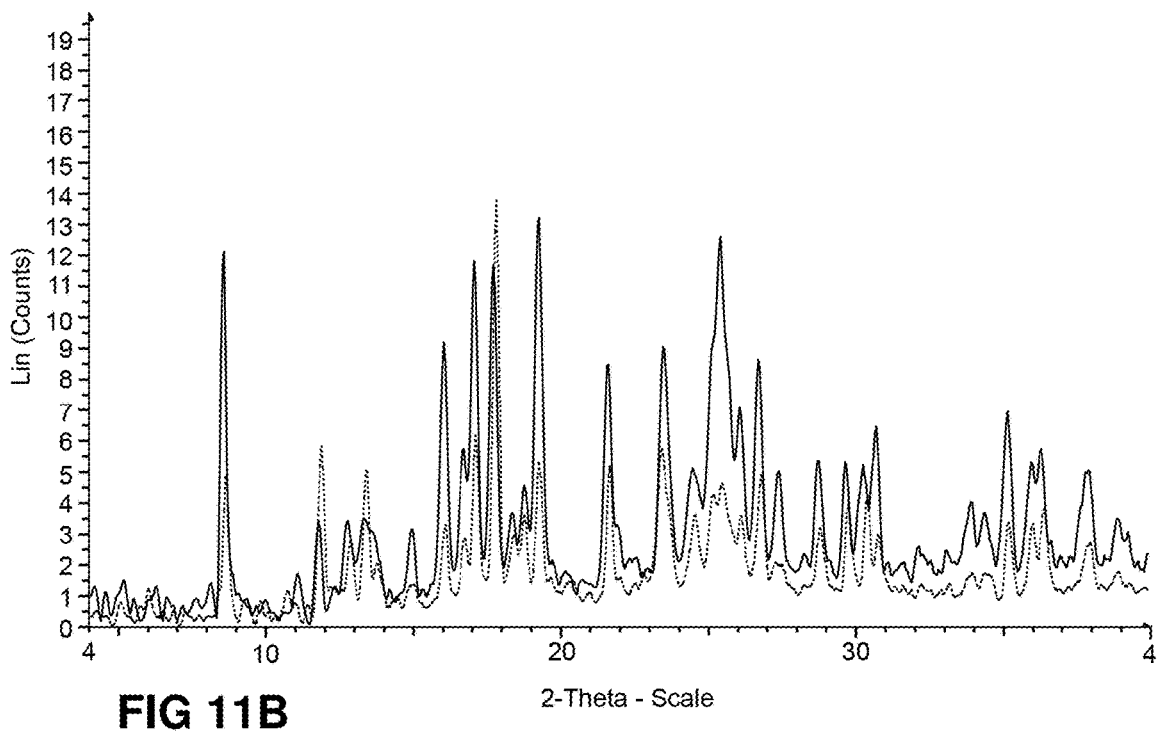
FIG. 11B shows the XRD spectrum of crystalline Form I J147.

Form I (Group B): The characteristic diffraction behavior of this form is shown in FIG. 1. The XRD patterns of the Form I samples were all crystalline and very similar. This form was obtained from a variety of solvents in approximately 50% of the experiments. The DSC profile of the Form I samples exhibited a melting endotherm with an onset of approximately 63° C. In all but one of the Form I samples analyzed, the endotherm was split with peak maximums ranging from approximately 67° C. to 75° C. This split endotherm is believed to be due to a mixture of two polymorphic forms as observed by hot stage microscopy. A representative DSC thermogram is shown in FIG. 2A. A sample of Form I exhibited a single endotherm in the DSC profile with an onset of melting at approximately 63° C. The XRD pattern matched that of the other Form I samples. FIGS. 11A and 11B show the DSC and XRD profiles, respectively, of this sample. The scanning TGA thermogram of Form I (FIG. 2B) showed it to be free from volatiles with a weight loss of less than 0.4 weight % from 25° C. to 104.7° C.

Figure 12A:
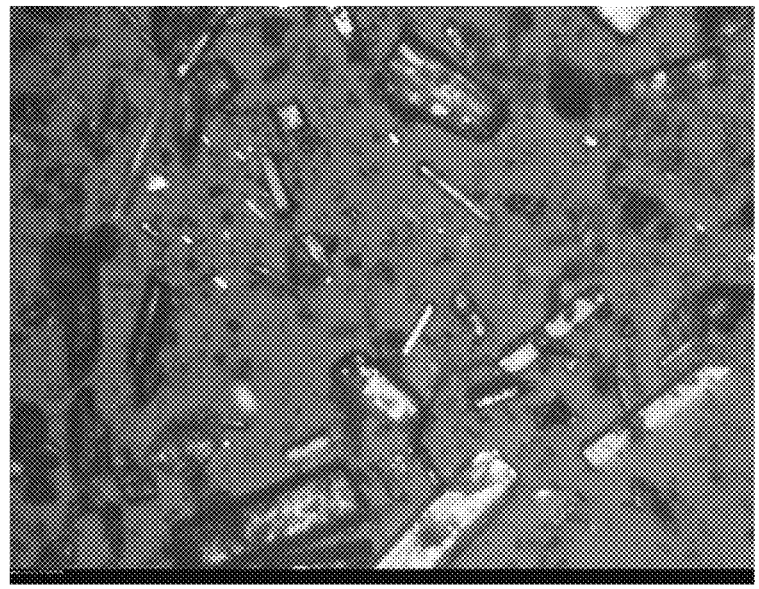
FIG. 12A shows a representative photomicrograph of crystalline Form I J147.
Figure 12B:
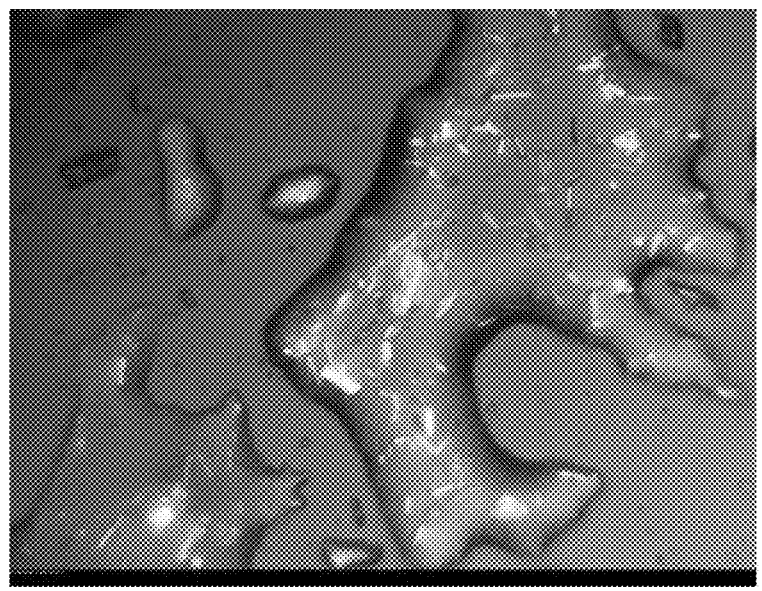
FIG. 12B shows another representative photomicrograph of crystalline Form I J147.

Microscopic evaluation of Form I showed a mixture of columnar and needle shaped particles ranging from approximately 10 to 300 microns in length. Upon heating this sample, the larger particles appear to melt at approximately 67° C., with the smaller needles unmelted. FIGS. 12A and 12B show representative photomicrographs at room temperature and 67° C. This along with the multiple endotherms in the DSC profile suggests the majority of the Form I samples may actually be a mixture of Forms I and II.

The dynamic vapor sorption isotherms and the kinetic plots for a representative sample of Form I are shown in FIGS. 3A and 3B, respectively. The material is very hydrophobic and does not appear to be prone to hydrate formation. A total weight loss of approximately 0.5% was observed at 95% RH. This unusual event (weight loss with high humidity) is most likely due to differences in the adsorption characteristics of the sample and reference pans and not the J147 sample. A sample of Form I was placed in a 40° C. in oven over weekend. XRD data showed a conversion to Form II. A variable temperature (VT) XRD experiment was performed on Form I. A sample of Form I was held in the XRD at 35° C. over a weekend with no form conversion observed. Overall, Form I was attributed to a dry crystalline, polymorphic form of the compound.

Figure 13:
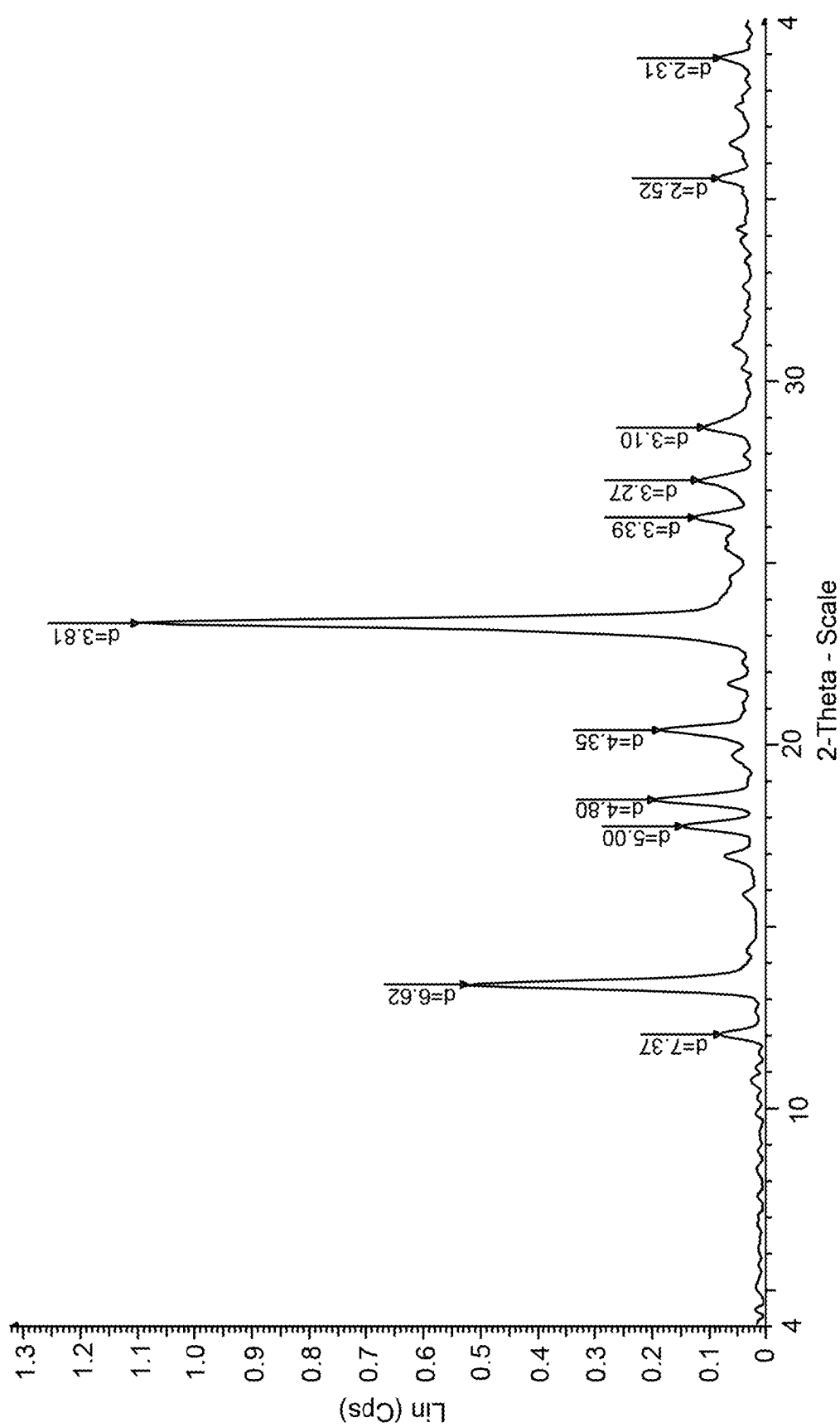
FIG. 13 shows the XRD spectrum of crystalline Form II J147.

Form II (Group A): The Form II polymorph was not obtained from the recrystallization screening experiments but was observed in approximately 50% of all experiments. The XRD patterns representative of Form II samples indicate that the samples were crystalline and very similar. FIG. 13 shows a characteristic XRD pattern of Form II. The peaks are summarized in Table C below.

TABLE C

| Angle 2-Theta ° | d value Angstrom | Intensity Cps | Intensity % |
|---|---|---|---|
| 12.00 | 7.37 | 0.08 | 6.9 |
| 13.37 | 6.62 | 0.52 | 47.4 |
| 17.74 | 5.00 | 0.14 | 13.1 |
| 18.47 | 4.80 | 0.19 | 17.4 |
| 20.39 | 4.35 | 0.18 | 16.7 |
| 23.34 | 3.81 | 1.10 | 100.0 |
| 26.25 | 3.39 | 0.12 | 11.0 |
| 27.28 | 3.27 | 0.12 | 10.5 |
| 28.74 | 3.10 | 0.11 | 9.6 |
| 35.60 | 2.52 | 0.08 | 7.3 |
| 38.91 | 2.31 | 0.08 | 7.0 |

Figure 14A:
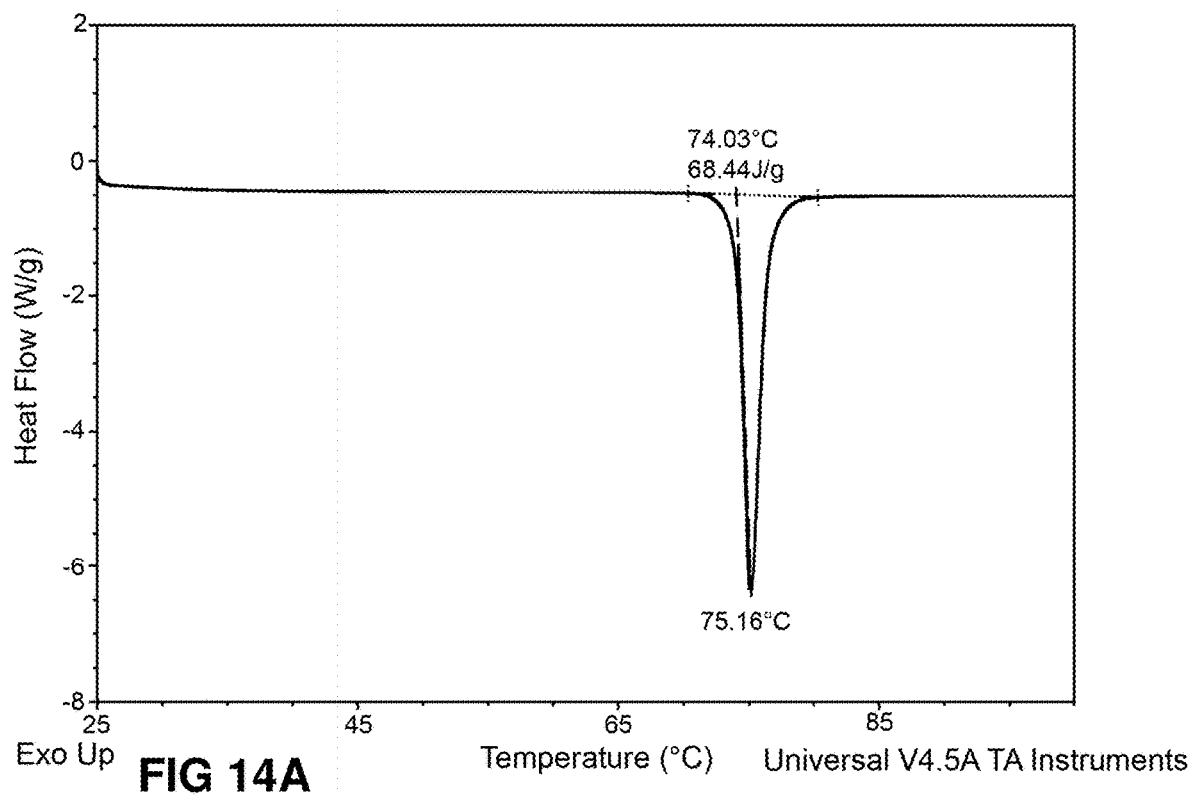
FIG. 14A shows a DSC thermogram of crystalline Form II of J147.
Figure 14B:
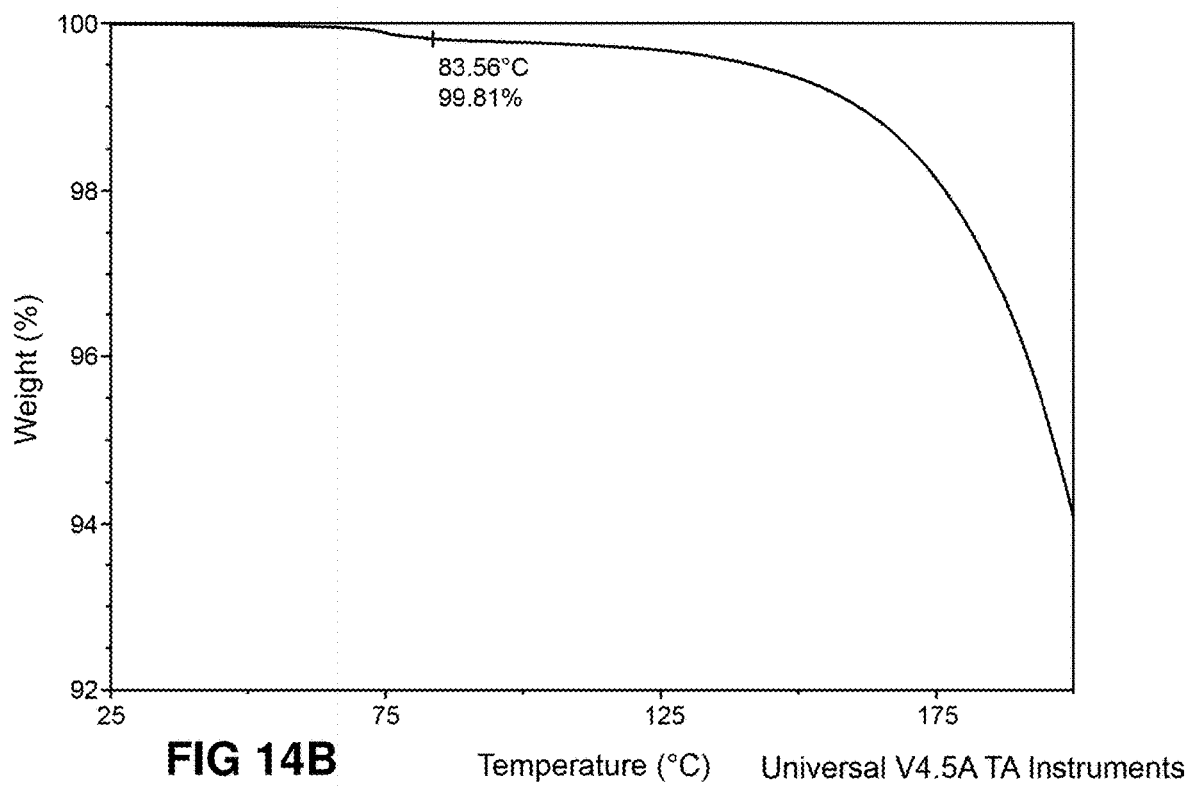
FIG. 14B shows a TGA thermogram of crystalline Form II of J147.
Figure 15:
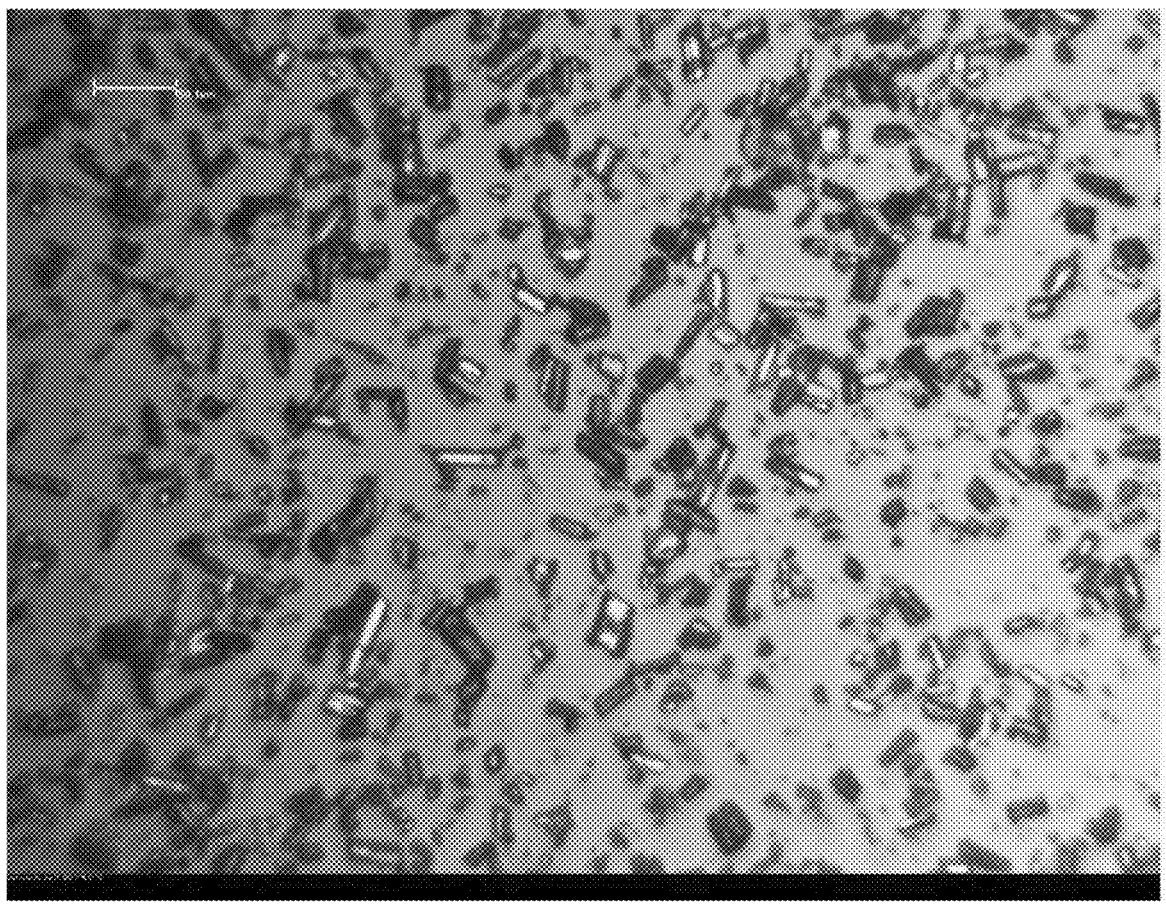
FIG. 15 shows a representative photomicrograph of crystalline Form II J147.
Figure 16A:
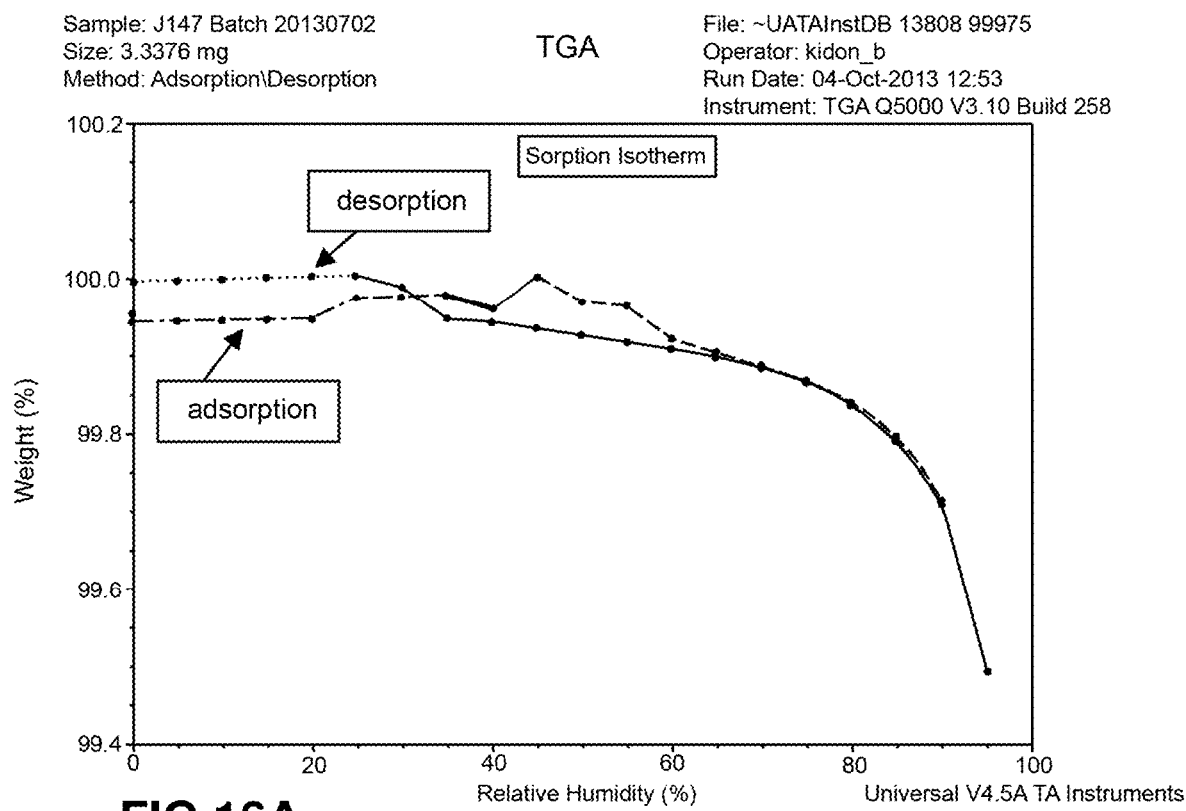
FIG. 16A shows the moisture sorption-desorption isotherm of crystalline Form II J147 using dynamic vapor sorption (DVS) analysis.
Figure 16B:
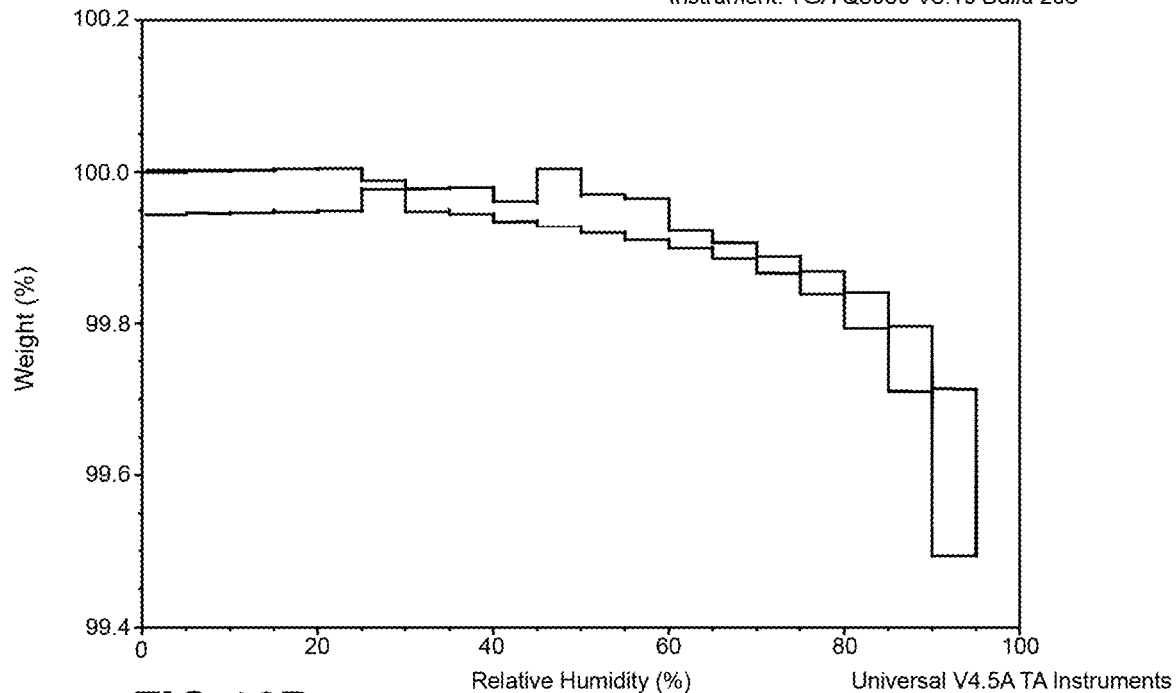
FIG. 16B shows kinetic plots of crystalline Form II J147 using DVS analysis.
Figure 17:
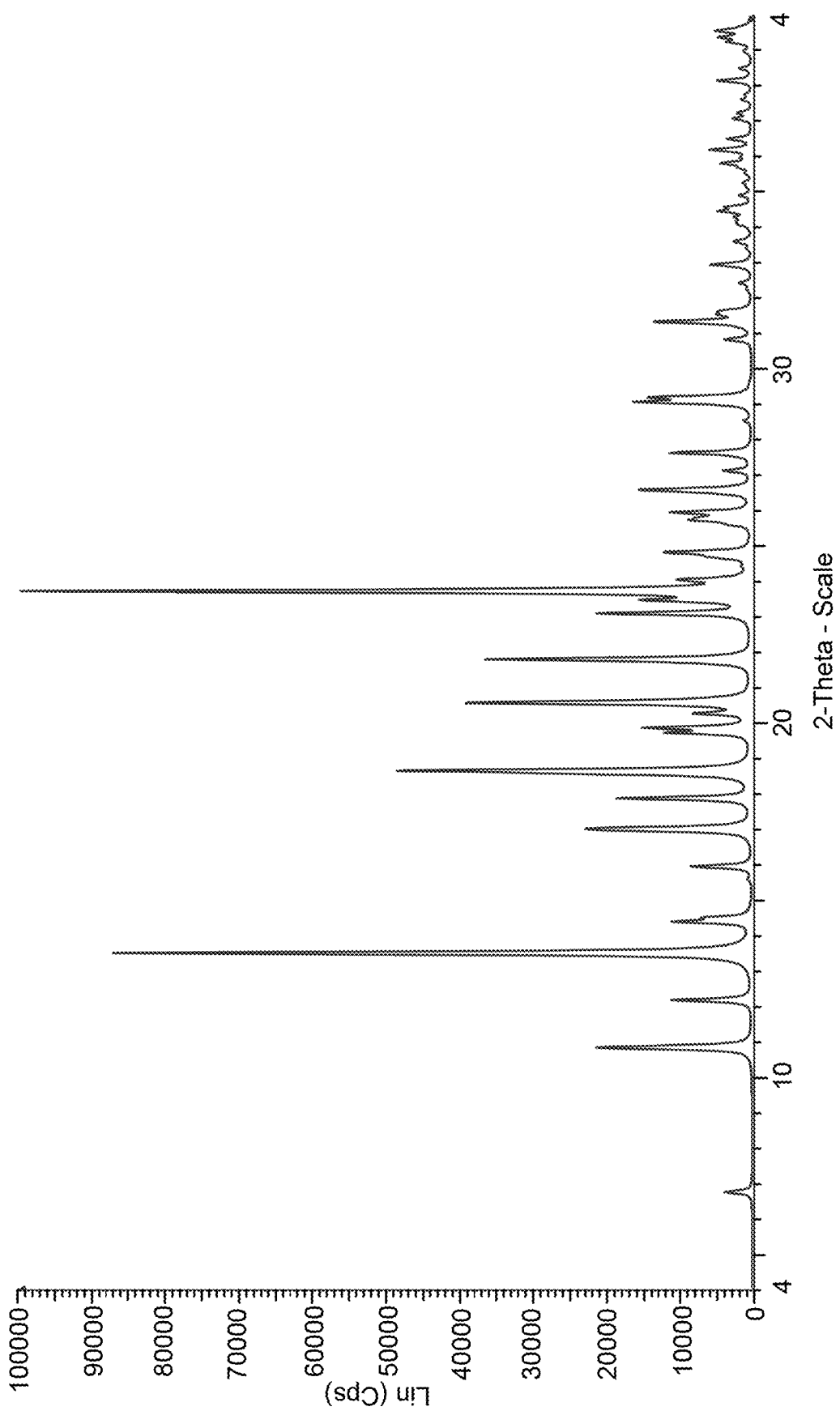
FIG. 17 shows a computer predicted powder XRD pattern of a single crystal of Form II of J147. The predicted pattern matched the pattern of experimental pattern.

The DSC thermograms of this form exhibit a well-defined melting endotherm with an extrapolated onset of approximately 74° C., a peak maximum of approximately 75° C. and an enthalpy of fusion of approximately 68 J/g. FIG. 14A shows the DSC profile of Form II. The TGA thermogram for Form II showed it to be free from volatiles with a weight loss less than 0.1% from 25° C. to 75° C. FIG. 14B shows the TGA profile. Microscopic evaluation of Form II showed birefringent needle shaped particles ranging from approximately 10 to 50 microns in length. FIG. 15 shows a representative photomicrograph of Form II crystals at room temperature. Upon heating, one melting event was observed at approximately 75° C. FIGS. 16A and 16B show the moisture sorption-desorption isotherm and the kinetic plots, respectively, for Form II. As seen with Form I, This form is also very hydrophobic and does not appear to be prone to hydrate formation A total weight loss of approximately 0.5% was observed at 95% RH. This unusual event (weight loss with high humidity) is most likely due to differences in the adsorption characteristics of the sample and reference pans and not the J147 sample. The single crystal predicted powder XRD pattern matched the pattern of experimental Form II as shown in FIG. 17. A sample of Form II was placed in a 40° C. in oven over weekend. XRD data showed no form conversion. Overall, Form II was attributed to a dry crystalline polymorphic form of the compound.

A number J147 samples were produced in this Example. The polymorph screen recrystallization experiments produced either Form I or an amorphous form of J147 (as shown in Table 11). The Form II polymorph was produced by creating a saturated slurry of Form 1 and agitating/stirring for several days at ambient temperature. Many of Form I samples also contained some amount of Form II indicating that the two polymorphs have a tendency to nucleate and grow concomitantly. Form II appears to be the thermodynamically stable form under ambient conditions based on the results of the competitive slurry experiments.

TABLE 11

| Panel No. | No. of Experiments | Form I | Amorphous |
|---|---|---|---|
| Panel 1 | 25 | 4 | 21 |
| Panel 2 | 27 | 12 | 15 |
| Panel 3 | 27 | 8 | 19 |
| Panel 4 | 27 | 3 | 24 |
| Panel 5 | 27 | None | 26 |
| Panel 6 | 15 | None | 13 |
| Total | 148 | 27 | 118 |
| % of total | 100% | 18% | 80% |

Competitive Slurry Experiments: In addition to the solvent recrystallization experiments, two competitive slurry experiments were also performed to determine the most stable form. These experiments rely on the solubility differences of different polymorphic forms. As such, only polymorphic forms (and solvates) having a lower solubility (more stable) than the form initially dissolved can result from a competitive slurry experiment.

The slurry experiments were performed by exposing excess material of Forms I and II to a small volume of solvent/water and agitating the resulting suspensions for several days at ambient temperature. The solids were filtered and analyzed by XRD and DSC to determine the resulting form. To avoid possible desolvation or physical change after isolation, the sample was not dried before x-ray analysis. Table 12 shows the results of the competitive slurry experiment.

TABLE 12

| Initial Forms (XRD) | Solvent | Slurry Duration | Final Form (XRD/DSC) |
|---|---|---|---|
| I & II | 1:1 ratio ethanol:water | 4 days | II |
| I & II | 1:1 ratio methanol:water | 8 days | II |

The competitive slurry experiments resulted in transformation of the sample to Form II. These results suggest that Form II is a less soluble, more thermodynamically stable polymorph relative to Form I at ambient temperature and pressure.

Grinding: Form I was ground using a Crescent Wig-L-Bug ball mill for 1 minute at 4800 oscillations per minute (3.2 m/s). XRD analysis showed no transformation under these conditions.

Recrystallization Using Heat: Amorphous/glass samples from Panel 1 were placed in a vacuum oven at 60° C. for 6 days. XRD analysis of these solids exhibited the XRD pattern of Form II. A sample of Form I was placed in a 40° C. in oven over a weekend. XRD data showed a conversion to Form II. A variable temperature (VT) XRD experiment was performed on Form I. A sample of Form I was held in the XRD at 35° C. over a weekend with no form conversion observed.

Thermodynamic Relationship: DSC experiments were performed in order to obtain heat of fusion and melting data. This data can often be used to determine if polymorphs exist in an enantiotropic or monotropic relationship. The heat of fusion rule states that, if the higher melting polymorph has the lower heat of fusion, the two forms are enantiotropes. Conversely, if the higher melting polymorph has a higher heat of fusion, the two forms are monotropes. For a monotropic system, any transition from one polymorph to another is irreversible. For an enantiotropic system, it may be possible to convert reversibly between the two polymorphs on heating and cooling.

A sample of pure Form I and two samples of Form II were analyzed by DSC at a slow heating rate of 2° C./minute with similar sample sizes. The average melting temperatures and heat of fusion data, from 10 runs, is shown in Table 13. These data indicate that Form I has a lower melting temperature and that Form II has a higher melting temperature. The heat of fusion values are very close with a high standard deviation for the Form I sample.

TABLE 13

| Sample ID | Onset (° C.) | Heat of Fusion (J/g) |
|---|---|---|
| Form I | 63.7 ± 0.4 | 71.5 ± 7.6 |
| Form II | 73.9 ± 0.1 | 70.3 ± 0.9 |

Static Vapor Sorption Study: A dynamic vapor sorption study was done in a sealed humidity chamber with an automatic moisture sorption balance. Data collected during dynamic vapor sorption studies often are not at thermodynamic equilibrium. To determine if the Form I and Form II material form a hydrate over time, samples were monitored in a 75% static humidity chamber.

In these studies, samples were stored in open Petri dishes in a chamber containing a saturated salt solution to maintain the relative vapor pressure. A solution of saturated sodium chloride (75% RH) salt at ambient temperature was used.

The samples were examined gravimetrically after 5 and 12 days. After both time periods, neither Form I nor II showed significant weight change, indicating no hydrate formation.

The raw diffraction data generated from the polymorph screening experiments were categorized into two polymorphic forms. Samples of these different forms were used to perform additional experiments (DSC, TGA, HSM, etc.) to refine the forms. A brief description of the discovered polymorphic forms is summarized in Table 14.

TABLE 14

| Form Designation | Description | Comments |
|---|---|---|
| Form I | Metastable | Pure Form I difficult to obtain. Tendency to nucleate and grow concomitantly with Form II. |
| Form II | Thermodynamically Stable | Good crystallinity and thermal properties. Form II readily obtained from solvent slurry and heat treatment of Form I. |

Table 14 summarizes the different solid state forms of J147 observed during the study. The main result is the discovery of two anhydrous polymorphic forms of J147. The polymorphic forms isolated in this Example were designated I and II. At room temperature and pressure Form II is the thermodynamically form of J147. Form I is the metastable form at room temperature and pressure.

Various experimental results have confirmed Form I is the metastable form at room temperature and pressure. Evidence of a transformation of Form I to Form II was observed after approximately 3 days of storage at 40° C. A competitive slurry of a 50/50 mix of Forms I and II in 2 different solvent systems (at ambient temperature) showed conversion of Form I to Form II after 4 and 8 days. Non-competitive slurry experiments of Form I in 7 different solvents systems showed conversion to Form II after 6 days.

The screen entailed subjecting the material to solvent crystallization, heating, grinding, sorption experiments, and competitive and noncompetitive slurry experiments. Overall, the J147 was recrystallized under more than 150 different crystal growth conditions and analyzed using powder x-ray diffraction. The x-ray data was used to categorize the samples into different groups. These groups were studied using thermal, optical, spectroscopic, and other tools to elucidate the unique solid state forms of the API. In general, the J147 exhibits two different polymorphic forms designated as Forms I and II in addition to the amorphous form. No solvates or hydrates were uncovered in this Example. Of the two polymorphic forms, the thermodynamically stable polymorph under ambient conditions was Form II.

Example of Preparation of Form II of J147

Batch Process: About 100 kg of crude J147 from its synthetic preparation was evaporated twice from about 80 kg of ethanol. The crude product was taken up in about 48 kg of ethanol and the batch temperature was adjusted to 28° C. About 37 kg of water was added gradually to the batch. The batch was held at about 30° C. for about 1.7 hours. A sample of the batch was pulled from the reactor and solids precipitated by addition of 45 mL of water. The solids obtained were added back to the batch as seed crystals and the mixture stirred for 40 minutes at 30° C. An additional about 34 kg of water was added. The batch was held at about 18° C. for about 58 hours and then cooled to about 10° C. for another about 5.5 hours. Analysis of the resultant solids indicated the presence of Form I. Form I was converted to Form II by heating the slurry to about 45° C. for about 16 hours and then cooling back to about 10° C. and holding the batch at this temperature for about 3 hours. about 17.7 kg of solid Form II of J147 were recovered by filtration after washing and drying.

What is claimed is:

1. A method of making crystalline Form II of 2,2,2-trifluoroacetic acid 1-(2,4-Dimethylphenyl)-2-[(3-methoxyphenyl)methylene]hydrazide (J147), having a powder X-ray diffraction pattern comprising peaks located at 13.37, 18.47, and 23.34+/−0.2 degrees 2-theta, the method comprising:
    (a) providing a slurry comprising saturated amorphous or crystalline Form I of 2,2,2-trifluoroacetic acid 1-(2,4-Dimethylphenyl)-2-[(3-methoxyphenyl)methylene] hydrazide (J147) in a mixture comprising a solvent and an anti-solvent; and
    (b) mixing the slurry to provide the crystalline Form II.

2. The method of claim 1, wherein the slurry comprises saturated J147 in the crystalline Form I.

3. The method of claim 1, wherein the mixing of (b) is carried out at a temperature in a range of about 25° C. to about 50° C.

4. The method of claim 1, wherein the mixing of (b) is carried out at a temperature in a range of about 40° C. to about 50° C.

5. The method of claim 1, wherein the anti-solvent is water.

6. The method of claim 1, wherein the solvent is an alcohol.

7. The method of claim 6, wherein the alcohol is selected from the group consisting of methanol, ethanol, trifluoroethanol, 1-propanol, and 2-propanol.

8. The method of claim 6, wherein the alcohol is ethanol.

9. The method of claim 1, wherein the solvent is dimethylformamide (DMF) or dimethylacetamide (DMA).

10. The method of claim 1, wherein the solvent is ethanol and the anti-solvent is water.

11. The method of claim 1, wherein a ratio of the solvent to the anti-solvent in the mixture is in a range from about 4:1 to about 1:4.

12. The method of claim 11, wherein a ratio is about 1:2.

13. The method of claim 1, wherein the mixing of (b) occurs over about 6 hours to about 6 days.

14. The method of claim 1, wherein a yield of the crystalline Form II is in a range from about 50% to about 100%.

15. The method of claim 1, wherein a purity of the crystalline Form II is at least 98%.

16. The method of claim 1, wherein the crystalline Form I of J147 has a powder X-ray diffraction pattern comprising peaks located at 11.85, 17.11, 17.79, and 23.40+/−0.2 degrees 2-theta, and is obtained by:
    recrystallizing 2,2,2-trifluoroacetic acid 1-(2,4-Dimethylphenyl)-2-[(3-methoxyphenyl)methylene]hydrazide from an organic solvent selected from the group consisting of nitromethane, methylethylketone, tetrahydrofuran, acetone, acetonitrile, heptane, isopropyl ether, isopropyl acetate, and chloroform, and optionally in the presence of water as an anti-solvent.

17. A method of making crystalline Form I of 2,2,2-trifluoroacetic acid 1-(2,4-Dimethylphenyl)-2-[(3-methoxyphenyl)methylene]hydrazide (J147), having a powder X-ray diffraction pattern comprising peaks located at 11.85, 17.11, 17.79, and 23.40+/−0.2 degrees 2-theta, the method comprising:
    recrystallizing 2,2,2-trifluoroacetic acid 1-(2,4-Dimethylphenyl)-2-[(3-methoxyphenyl)methylene]hydrazide from an organic solvent selected from the group consisting of nitromethane, methylethylketone, tetrahydrofuran, acetone, acetonitrile, heptane, isopropyl ether, isopropyl acetate, and chloroform, and optionally further comprising water as anti-solvent.

18. The method of claim 17, wherein the recrystallizing is performed with water as the anti-solvent and the ratio of organic solvent to anti-solvent is in a range from about 4:1 to about 1:4.

19. A method of making crystalline Form I of 2,2,2-trifluoroacetic acid 1-(2,4-Dimethylphenyl)-2-[(3-methoxyphenyl)methylene]hydrazide (J147), having a powder X-ray diffraction pattern comprising peaks located at 11.85, 17.11, 17.79, and 23.40+/−0.2 degrees 2-theta, the method comprising:

recrystallizing 2,2,2-trifluoroacetic acid 1-(2,4-Dimethylphenyl)-2-[(3-methoxyphenyl)methylene]hydrazide from a mixture comprising a solvent and an anti-solvent, wherein the solvent is an alcohol, and the anti-solvent is water or heptane.

20. Isolated crystalline Form I of 2,2,2-trifluoroacetic acid 1-(2,4-Dimethylphenyl)-2-[(3-methoxyphenyl)methylene]hydrazide (J147), having a powder X-ray diffraction pattern comprising peaks located at 11.85, 17.11, 17.79, and 23.40+/−0.2 degrees 2-theta, and wherein the powder X-ray diffraction pattern further comprises X-ray diffraction peaks located at 8.64, 13.36, 19.25, 21.64, and 26.81+/−0.2 degrees 2-theta.

21. Isolated crystalline Form II of 2,2,2-trifluoroacetic acid 1-(2,4-Dimethylphenyl)-2-[(3-methoxyphenyl)methylene]hydrazide (J147), having a powder X-ray diffraction pattern comprising peaks located at 13.37, 18.47, and 23.34+/−0.2 degrees 2-theta, and wherein the powder X-ray diffraction pattern further comprises X-ray diffraction peaks located at 17.74, 20.39, 26.25, 21.64, and 28.74+/−0.2 degrees 2-theta.

* * * * *